(12) United States Patent
Ninomiya et al.

(10) Patent No.: US 8,412,298 B2
(45) Date of Patent: Apr. 2, 2013

(54) PROBE DEVICE

(75) Inventors: Atsushi Ninomiya, Ome (JP); Yoshimi Kasai, Nagareyama (JP)

(73) Assignee: Hitachi, Ltd., Tokyo (JP)

( * ) Notice: Subject to any disclaimer, the term of this patent is extended or adjusted under 35 U.S.C. 154(b) by 1113 days.

(21) Appl. No.: 12/323,582

(22) Filed: Nov. 26, 2008

(65) Prior Publication Data

US 2009/0247839 A1  Oct. 1, 2009

(30) Foreign Application Priority Data

Mar. 31, 2008 (JP) ................................. 2008-089135

(51) Int. Cl.
*A61B 5/00* (2006.01)
(52) U.S. Cl. ........................................ 600/344; 600/310
(58) Field of Classification Search .................. 600/340, 600/344
See application file for complete search history.

(56) References Cited

U.S. PATENT DOCUMENTS

| | | | |
|---|---|---|---|
| 5,038,782 A | 8/1991 | Gevins et al. | |
| 7,039,454 B1 | 5/2006 | Kaga et al. | |
| 7,139,600 B2 * | 11/2006 | Maki et al. | 600/344 |
| 7,280,859 B2 * | 10/2007 | Maki et al. | 600/344 |

FOREIGN PATENT DOCUMENTS

| | | |
|---|---|---|
| JP | 9-140715 A | 6/1997 |
| JP | 2001-286449 | 10/2001 |
| JP | 2002-011012 A | 1/2002 |
| JP | 2002-355246 A | 12/2002 |
| JP | 2004-073559 A | 3/2004 |
| JP | 2004-097590 A | 4/2004 |
| JP | 2006-122458 A | 5/2006 |
| JP | 2007-227388 A | 9/2007 |

* cited by examiner

*Primary Examiner* — Jeffrey G Hoekstra
*Assistant Examiner* — H. Q. Nguyen
(74) *Attorney, Agent, or Firm* — Mattingly & Malur, PC

(57) ABSTRACT

In a probe device including a light irradiating portion irradiating a light to a surface of a living body, and a light detecting portion detecting the light passing through an inner portion of the living body so as to emit from the surface of the living body, the probe device is provided with a sheet-like probe holding body, a plurality of light emitting probes and a plurality of detection probes which are attached to the probe holding body at a predetermined interval, a board holding portion attached to a predetermined position of the probe holding portion, an electronic board attached to the board holding portion, a sheet holding portion holding the probe holding body at a predetermined position of a head portion (a tested position) of the test subject, and a fixing band portion for installing the sheet holding portion to the test subject.

9 Claims, 11 Drawing Sheets

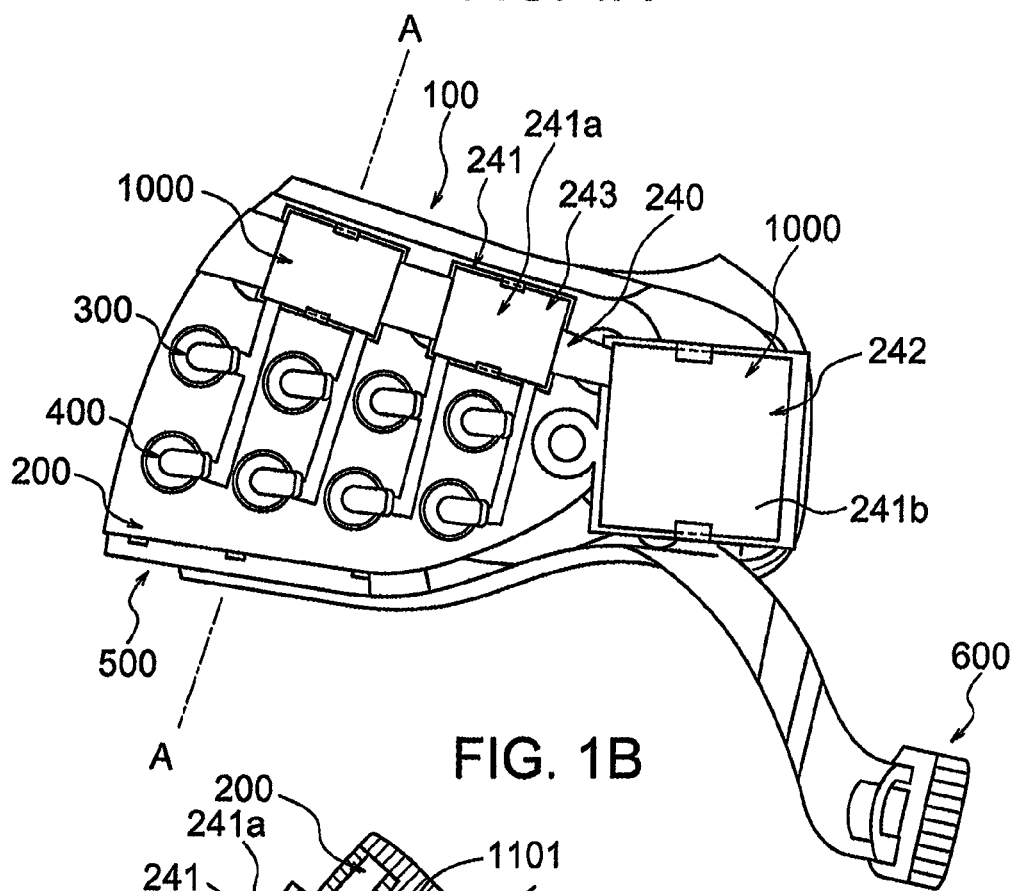
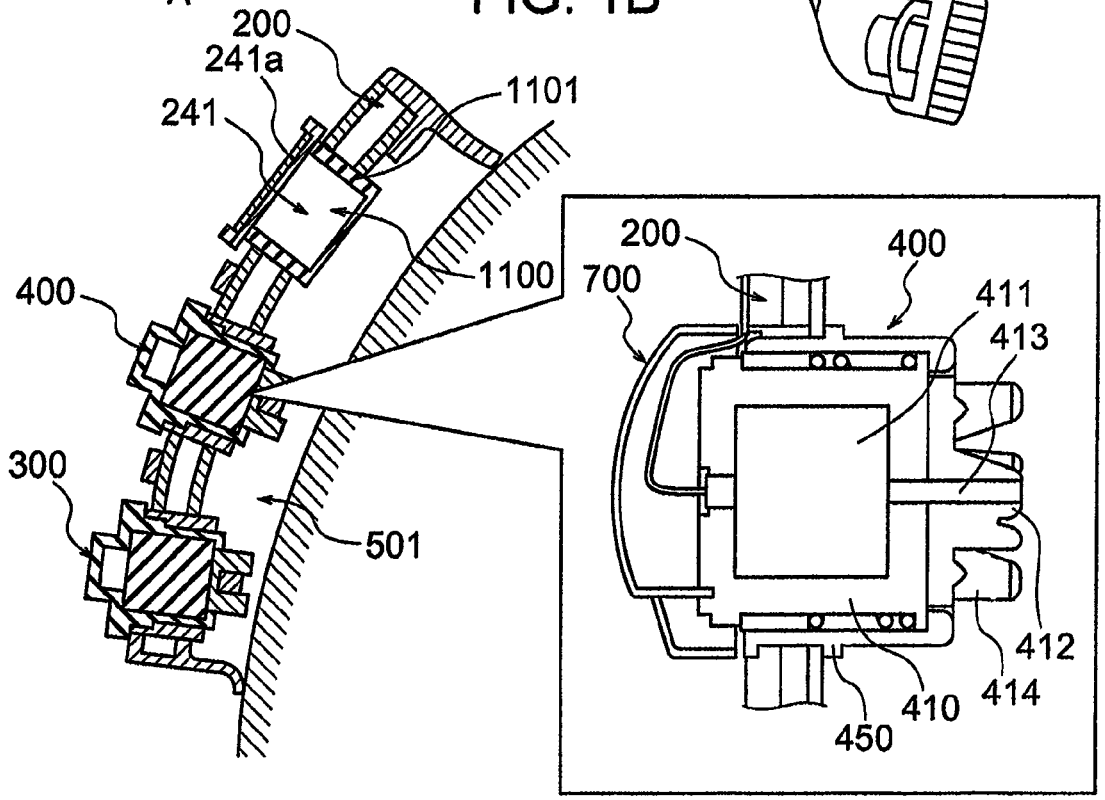

PROBE DEVICE

CLAIM OF PRIORITY

The present application claims priority from Japanese patent application JP2008-089135 filed on Mar. 31, 2008, the content of which is hereby incorporated by reference into this application.

BACKGROUND OF THE INVENTION (1) Field of the Invention

The present invention relates to a probe device for a biological light measuring device, and more particularly to a probe device for a biological light measuring device which is preferably used for measuring a local blood dynamic change in a living body.

(2) Description of Related Art

As a biological light measuring device, there has been known a measuring device called a light topography device (for example, JP-A-2001-286449). This device is structured such that a probe device in which a lot of probe main bodies having a light irradiation and detection portion are arranged is attached so that each of the probe main bodies is closely attached to a measured position, for example, a head portion, and a measurement is carried out by irradiating a near infrared ray from each of the probe main bodies.

A probe device in accordance with a prior art is structured by arranging a plurality of probe main bodies in a grid-like manner in a shell portion constructed by a sheet material formed as a bowl shape in correspondence to a shape of a head portion of a test subject. Each of the probe main bodies is detachable from the shell portion, and in the case that an incompleteness of a contact of the probe main body with a scalp due to hair or the like is confirmed by a monitor screen, it is possible to reinstall only the probe in this portion. Since the probe device structured as mentioned above is not necessarily fit to the head portion due to an individual difference of the head portion shape of the test subject and a difference of the installed position in the case that it is installed at the head portion of the test subject, the probe device is used by hanging a fixing belt to a jaw so as to firmly press the shell portion to the head portion. Further, in the case of measuring, the structure is made such as to irradiate the near infrared ray transmitted via each of optical fibers toward a subcutaneous part of the head portion via a light emitting probe main body, receive a reflected light by a light receiving probe main body, and retransmit to the measuring device main body via the optical fiber.

In the probe device in accordance with the prior art mentioned above, the light emitting portion irradiating the light with respect to the shell portion and the detection portion are alternately arranged in the grid-like manner, and each of the light emitting portion and the detection portion is provided with a structure supplying the light via the optical fiber or collecting the detected light via the optical fiber. Accordingly, for the test subject with the probe device installed at the head portion, since a plurality of fibers are attached around the head portion, there is a problem that freedom of behavior of the test subject is obstructed, or a sense of insecurity is present in the test subject.

BRIEF SUMMARY OF THE INVENTION

An object of the present invention is to provide a probe device which can achieve a high-precision measurement without being affected by heat generation of a control board, and has a good weight balance and a good installing property with respect to a test subject.

In order to achieve the object mentioned above, in accordance with the present invention, there is provided a probe device including a light irradiating portion irradiating a light to a surface of a living body, and a light detecting portion detecting the light passing through an inner portion of the living body so as to emit from the surface of the living body, wherein the probe device includes a sheet-like probe holding body, a plurality of light emitting probes and a plurality of detection probes which are attached to the probe holding body at a predetermined interval, a board holding portion attached to a predetermined position of the probe holding portion, an electronic board attached to the board holding portion, a sheet holding portion holding the probe holding body at a predetermined position with respect to a head portion of the test subject, and a fixing band portion for installing the sheet holding portion on the test subject, the electronic board including a plurality of probe control boards controlling respective motions of a plurality of light emitting probes and a plurality of detection probes within a predetermined region, and a main control board generally controlling a plurality of probe control boards and communicating with the other devices, the board holding portion including a first board holding portion for attaching the probe control board, and a second board holding portion for attaching the main control board.

In the probe device in accordance with the present invention, it is preferable that the probe holding body is provided with hole portions formed per a predetermined interval, and the light emitting probes, the detection probes and the board holding portion are detachably fitted to the hole portions.

In the probe device in accordance with the present invention, it is preferable that the main control board has a communication means making it possible to communicate wirelessly with a biological light measuring device main body image means processing an electric signal output from the probe device so as to display a map or the like.

In the probe device in accordance with the present invention, it is preferable that the main control board is provided in an end portion of the probe holding body.

In the probe device in accordance with the present invention, it is preferable that the probe device is provided with an electronic board having a power source portion supplying a power source to the probe device.

In the probe device in accordance with the present invention, it is preferable that the main control board and the electronic board are arranged so as to oppose to each other.

In the probe device in accordance with the present invention, it is preferable that the probe device has a sheet holding portion holding the probe holding portion at a predetermined position with respect to a surface of the living body, the sheet holding portion surrounds a periphery of the probe holding body, and forms a shielding space shielded light while being provided with a predetermined gap between the probe holding body and the surface of the living body.

In the probe device in accordance with the present invention, it is preferable that a plurality of light emitting probes and a plurality of detection probes are provided with a probe main body including a light emitting unit or a detection unit, and a probe attaching portion detachably attaching the probe main body to a predetermined position of the probe holding body, and the probe attaching portion is held so as to freely rotate the probe main body around a main projection portion in such a manner that one end provided with the main projection portion and a sub-projection portion is exposed to the shielding space and the other end is exposed to an outer side of the probe holding body.

In the probe device in accordance with the present invention, it is preferable that a wiring sheet is arranged in such a manner as to be laminated on the probe holding body, and is provided with a protection cover covering the probe holding body in a state in which the probe control board, the control board and the wiring sheet are attached.

In the probe device in accordance with the present invention, it is possible to provide a probe device which can achieve a high-precision measurement without being affected by the heat generation of the control board, and has a good weight balance and a good installing property with respect to the test subject.

Other objects, features and advantages of the invention will become apparent from the following description of the embodiments of the invention taken in conjunction with the accompanying drawings.

BRIEF DESCRIPTION OF THE SEVERAL VIEWS OF THE DRAWINGS

FIGS. 1A and 1B are schematic views of an outline structure of a probe device;

DETAILED DESCRIPTION OF THE INVENTION

Figure 2:
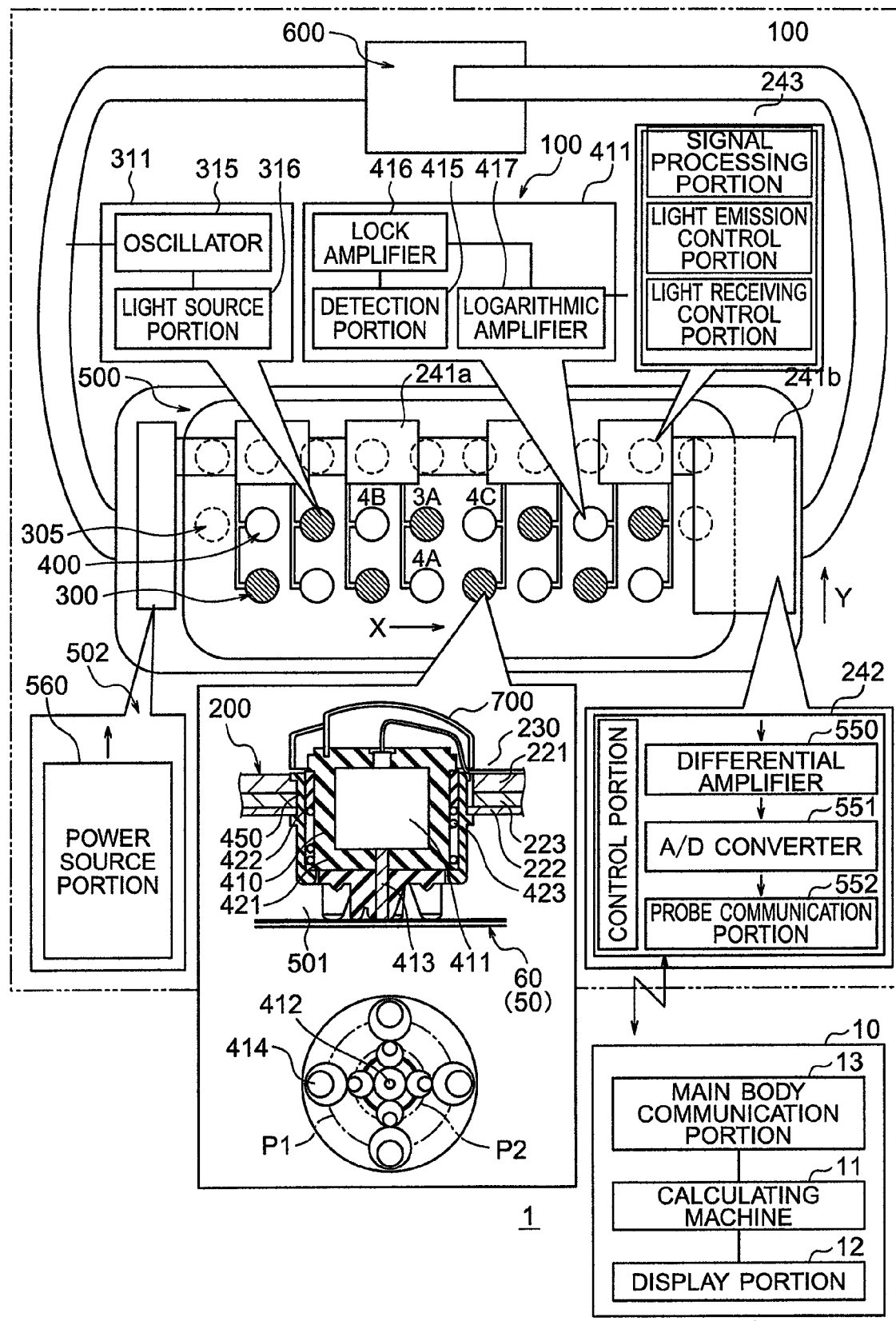
FIG. 2 is a schematic view of an outline structure of a biological light measuring device.

A description will be specifically given below of a biological light measuring device in accordance with an embodiment with reference to FIGS. 1 (1A and 1B) to 11 (11A and 11B). The biological light measuring device in accordance with this embodiment is a device for measuring a local blood dynamic change in a living body by utilizing a matter that if a certain portion of a brain is activated, an amount of blood for feeding oxygen to the portion is increased accordingly. Specifically, it is possible to simply observe a function of the brain by measuring a change of the amount of blood near a surface of a cerebrum by irradiating a near infrared ray from above a scalp and measuring a scattering generated by hemoglobin in the blood by means of the near infrared ray, and expressing the change in a two-dimensional map or the like. In this case, the near infrared ray means an electromagnetic wave in a region in which the wavelength is longer than visible light.

First of all, a description will be given of an outline structure of a probe device of a biological light measuring device in accordance with this embodiment with reference to FIG. 1. In this case, FIGS. 1A and 1B are views of the outline structure of the probe device in accordance with this embodiment, in which FIG. 1A is a perspective view of an outer appearance of the probe device, and FIG. 1B is a cross-sectional view of a portion along a broken line A-A in FIG. 1A.

In FIGS. 1A and 1B, a probe device 100 in accordance with the embodiment is structured such as to include a sheet-like probe holding body 200, a plurality of light emitting probes 300 and a plurality of detection probes 400 which are attached to the probe holding body 200 at predetermined intervals, a board holding portion 241 attached to a predetermined position of the probe holding body 200, an electronic board 1000 attached to the board holding portion 241, a sheet holding portion 500 holding the probe holding body 200 at a predetermined position with respect to a head portion (a testing position) of a test subject, and a fixing band portion 600 for installing the sheet holding portion 500 to the test subject.

The electronic board 1000 is structured such as to include a plurality of probe control boards 243 controlling a motion of each of a plurality of light emitting probes 300 and a plurality of detection probes 400 in a predetermined region, and a main control board 242 generally controlling a plurality of probe control boards 243 and communicating with the other devices, and the board holding portion 241 is accordingly prepared with a first board holding portion 241a for attaching the probe control boards 243, and a second board holding portion 241b for attaching the main control board 242 and a power source portion (not shown). In this case, a plurality of probe control boards 243 and the main control board 242 are connected by a wiring sheet 240 in an operable manner.

In this embodiment, a plurality of light emitting probes 300 and a plurality of detection probes 400 are arranged in a lower portion of the probe holding body 200 having a wide shape, the first board holding portion 241a provided with a plurality of probe control boards 243 is arranged in an upper portion thereof, and the second board holding portion 241b for attaching the main control board 242 and another power source portion 560 (refer to FIG. 2) is arranged on both sides of the probe holding body 200. Further, the wiring sheet 240 has a wiring function including a wiring of a signal and a wiring of the power source, and the wiring sheet 240 can be incorporated in an inner portion of a laminated member.

The probe holding body 200 is a laminated member in which a plurality of sheet materials are laminated, and is provided with a flexible holding function capable of maintaining attitudes of the light emitting probes 300 and the detection probes 400, and a light shielding function preventing an outside light from making an intrusion into the head portion.

In other words, the probe holding body 200 supports a plurality of light emitting probes 300 and a plurality of detection probes 400 so as to be arranged alternately and in a matrix shape onto a plane thereof, in such a manner as to position the detection probes 400 on both sides next to the light emitting probes 300, and boards controlling each of the light emitting probes 300 and the detection probes 400 are arranged at upper positions thereof. Further, the probe holding body 200 is provided with suitable flexibility and strength for holding attitudes of these two kinds of probes, prevents an outside light from making an intrusion into the tested portion, and secures breathability for perspiration.

The light emitting probes 300 and a plurality of detection probes 400 are provided with the same structure as shown in a balloon in the lower right side of FIG. 1B. In this case, the description is given while focusing on the structure of the detection probe 400, and the light emitting probe 300 will be described mainly about the difference from the detection probe 400.

As shown in the balloon in the lower right side of FIG. 1B, the detection probe 400 is constructed of a detection probe main body 410 provided with a detection unit 411, and a detection probe attaching portion 450 attaching the detection probe main body 410 to the predetermined position of the probe holding body 200. On the other hand, the light emitting probe 300 is constructed by a light emitting probe main body 310 provided with a light emitting unit 311 having the same structure as the detection unit 411, and a light emitting probe attaching portion 350 attaching the light emitting probe main body 310 to the predetermined position of the probe holder 200. Further, the detection probe main body 410 and the light emitting probe main body 310 have a cap portion 700 provided with the same structure attached covering an exposed surface thereof. In this case, the cap portion 700 may be given coloring differently for differentiating the functions.

Each of the detection probe main body 410 and the light emitting probe main body 310 is provided with a main projection portion 412 in the test subject side, and is provided with an optical fiber 413 communicating a leading end of the main projection portion 412 with the detection unit 411 or the light emitting unit 311. Further, in this embodiment, there is employed a structure in which a plurality of sub-projection portions 414 are arranged around the main projection portion 412. Further, the light emitting probe 300 is also provided with the main projection portion 412 having the optical fiber 413 for irradiating in a contact surface 60 with the test subject 50 in the same manner, and employs a structure of "surface contact constituted by a plurality of points" in which a plurality of sub-projection portions 414 are arranged around the main projection portion 412.

Further, the detection probe main body 410 and the light emitting probe main body 310 are attached to the detection probe attaching portion 450 or the light emitting probe attaching portion 350 so as to be rotatable around the main projection portion 412. In accordance with a plurality of sub-projection portions 414 and a rotational structure, it is possible to achieve a function of pushing the hair of the test subject aside, and an attitude control of the probe itself.

Further, the board holding portion 241 is structured such as to include a board holding portion main body 1100 detachably holding the electronic board 1000, and a board attaching portion 1101 attached to the probe holding portion 200 and detachably supporting the board holding portion main body 1100.

Further, one of the great features of the probe device in accordance with this embodiment consists of employing a sheet holding portion 500 holding a periphery of the sheet-shaped probe holding body 200, maintaining a predetermined interval between the probe holding body 200 and the scalp of the test subject, and securing a light shielding space 501 which shields light by the probe holding body 200 and the scalp of the test subject. In accordance with the embodiment forming the light shielding space 501, it is possible to secure a sufficient space to change the attitudes of the detection probe main body 410 and the light emitting probe main body 310, and a sufficient space to secure breathability for perspiration. Further, since the sheet holding portion 500 is formed by a soft material such as rubber or the like, it is easy to install on the test subject.

Further, another of the great features of the probe device in accordance with this embodiment is that the probe device 100 is provided with the electronic board 1000 and a power source portion 560 (refer to FIG. 2). In other words, this embodiment has the main control board 242, and an electronic board having a power source function shown in FIG. 2 in a side surface on an opposite side thereto. Further, the main control board 242 has a differential amplifier, an A/D converter, a probe communication portion, a control portion and the like built-in. Accordingly, since a standby state can be achieved by installing the probe device, it is possible to improve correspondence. Further, since the electronic board 1000 such as the probe control boards 243, the main control board 242 and the like is arranged in such a manner as to surround the periphery of the probe holding portion 500, it is possible to achieve a weight balance and it is possible to achieve the probe device having an improved installing property.

Further, another one of the great features of the probe device in accordance with this embodiment is that the light emitting probe main body 310, the detection probe main body 410, the electronic board 1000 and the like are detachably attached to the probe holding body 200. In other words, the light emitting probe main body 310, the detection probe main body 410 and the electronic board 1000 are detachably attached to the probe holding body 200 via the light emitting probe attaching portion 350, the detection probe attaching portion 450 and the board attaching portion 1101. Particularly, in this embodiment, the board attaching portion 1101 has a the structure having the same shape as the light emitting probe attaching portion 350 and the detection probe attaching portion 450, and an arrangement of the board attaching portion 1101 is part of a matrix-shaped arrangement of light emitting probe attaching portions 350 and detection probe attaching portions 450.

Therefore, in accordance with this structure, it is possible to attach the electronic board 1000 by attaching the board holding portion main body 1100 in place of a light emitting probe main body 310 or a detection probe main body 410. Of course, the board holding portion main body 1100 may be independently provided.

A description will be given below in further detail of the testing device in accordance with this embodiment. In this case, the same positions and the same arrows are shown by the same reference numerals, and an overlapping description will be omitted.

First of all, a description of an outline structure of a biological light measuring device in accordance with a first embodiment is given with reference to FIG. 2. In this case, FIG. 2 is a schematic view of the outline structure of the biological light measuring device.

In FIG. 2, the biological light measuring device generally denoted by reference numeral 1 is structured such as to include a probe device 100 installed at a head portion of a test subject, and a biological light measuring device main body 10 image processing an electric signal output from the probe device 100 so as to display a map or the like. As mentioned above, the probe device 100 in accordance with this embodiment is structured such as to include a sheet-like probe holding body 200, a plurality of light emitting probes 300 and a plurality of detection probes 400 which are attached to the probe holding body 200 at predetermined intervals, a board holding portion 241 attached to a predetermined position of the probe holding body 200, an electronic board 1000 attached to the board holding portion 241, a sheet holding portion 500 holding the probe holding body 200 at a predetermined position with respect to a head portion (a testing position) of a test subject, and a fixing band portion 600 for installing the sheet holding portion 500 on the test subject. Further, the electronic board 1000 is constructed by a plurality of probe control boards 243 controlling a motion of each of a plurality of light emitting probes 300 and a plurality of detection probes 400 in a predetermined region, and a main control board 242 generally controlling a plurality of probe control boards 243 and communicating with the other devices, and the board holding portion 241 is accordingly prepared with a first board holding portion 241a for attaching the probe control boards 243, and a second board holding portion 241b for attaching the main control board 242 and a power source portion 560.

In this embodiment, the probe device 100 is structured such as to be provided with a "goggle-shaped" outer appearance by forming the probe holding body 200 in an approximately wide rectangular shape, surrounding a periphery of the probe holding body 200 by a thick (deep) sheet holding portion 500, and attaching a fixing band portion 600 in both ends in a longitudinal direction of the sheet holding portion 500. Further, in accordance with this embodiment, the probe holding body 200 is pressed and set to the head portion of the test subject in a direction in which a longitudinal direction of the probe holding body 200 comes to a side attitude of the head portion of the test subject. In this attitude, the probe holding body 200 is set to a predetermined position with respect to the head portion of the test subject with a predetermined gap via the sheet holding portion 500 while securing the light shielding space 501 in which the light is shielded. Further, since the sheet holding portion 500 is formed by a flexible material, the sheet holding portion 500 can be formed as a curved shape in correspondence to an approximately spherical shape of the head portion of the test subject. Accordingly, it is possible to fit the probe holding body 200 to the head portion of the test subject. Further, since the fixing band portion 600 is provided with an existing structure which can be adjusted in length, it is possible to set the probe device 100 to the predetermined position with respect to the head portion of the test subject in correspondence to a body type of the test subject.

Further, the sheet holding portion 500 is provided with an electronic board 502 on one side surface in a longitudinal direction, and a main control board 242 on an opposite side surface. In other words, as shown in a balloon in the left lower side of FIG. 2, the electronic board 502 is provided with a power source portion 560, and the main control board 242 is provided with at least a differential amplifier 550, an A/D converter 551, a probe communication portion 552, and a control portion. In this embodiment, there is employed a wiring sheet 240 connecting the main control board 242, the probe control board 243 and the electronic board 502 in such a manner as to be laminated by the probe holding body 200. The wiring sheet 240 is constructed by a plurality of band-shaped sheets, and is wired so as to creep between the light emitting probe 300 and the detection probe 400 which are arranged so as to be fitted to a hole portion 305 arranged in the matrix shape in the probe holding body 200. Further, each of the light emitting and light receiving probes is structured such that the wiring sheet 240 is wired from a probe control board 243 held by a first board holding portion 241a attached to a hole portion 305 in an upper stage than each of the arranged probes.

In this embodiment, the wiring sheet 240 is provided with a structure which is divided into right and left with respect to a center line extending in a vertical direction of the probe holding body surface, the probe control board 243, the light emitting probe 300 and the detection probe 400 are connected by the wiring sheet 240, and the probe control board 243 is connected to the electronic board 502 and the main control board 242 arranged on both sides by the wiring sheet 240. At this time, it goes without saying that a length from each probe control board 243 of the wiring sheet 240 to each of the light emitting and light receiving probes has a sufficient length to reach each of the probes, however, in order to prevent a disconnection while taking into consideration an attachment and detachment of the probe device, a motion of the test subject and the like, it is necessary to sufficiently secure an extra length in such a manner as to provide a so-called play in the probe control boards 243 and the main control board 242.

In this case, in this embodiment, the light emitting probes 300 and the detection probes 400 which are arranged in the matrix shape are divided into up and down, and are wired to the probe control boards 243 arranged in the vicinity of the upper portion of the wiring sheet 240 by a pair of upper and lower wiring sheets 240, however, the structure is not limited to this. For example, the structure may be made such that the light emitting probes 300 and the detection probes 400 are separated, and are wired right and left, or they may be separated into right and left per one row so as to be wired. Further, there is employed the structure in which the detection and light emitting probes are arranged in the matrix shape in the hole portions formed in two rows and eight columns, however, the structure is not limited to this, but the probes can correspond to the hole portions in more rows and more columns. In this case, with regard to the probe control boards, there is employed a structure in which the probe control boards 243 are sequentially arranged per two rows and two columns, however, the number of the boards is not limited to this.

Further, in this embodiment, the electronic board 502 is provided in the sheet holding portion 500, however, the electronic board 502 may be provided in an independent holder board portion connected via a cord.

On the other hand, a plurality of light emitting probes 300 and a plurality of detection probes 400 are arranged alternately and in a matrix shape in such a manner as to position the detection probes 400 on both sides next to the light emitting probes 300 shown by a hatched lines. Accordingly, the light irradiated from one light emitting probe can be detected by detecting units 411 of three detection probes 4A, 4B and 4C arranged on both sides in an X direction and a Y direction. In other words, one detection probe 400 can detect the light irradiated from three light emitting probes 300 which are arranged on both sides in the X direction and the Y direction. In other words, in accordance with this embodiment, it is possible to measure a blood dynamic change in a whole of the region to which the probe device 100 is installed. The signal detected here is transmitted to the main control board 242 via a signal processing portion and a control portion within the probe control board 243 corresponding to each of the probes, and is transmitted to the main body 10 via the main control board 242. Further, with regard to the input signal from the main body 10, the signal is transmitted to each of the probes in accordance with the flow mentioned above, and the motion is controlled.

Further, the light emitting probe 300 and the detection probe 400 are provided with the same structure, as shown in a balloon in a lower side of FIG. 2. In this case, a description will be given while focusing on the structure of the detection probe 400, and the light emitting probe 300 will be described mainly about the difference from the detection probe 400.

The light emitting unit 311 is provided with a light source portion 316 shown in the balloon in the left upper side of FIG. 2 and an oscillator 315 for removing noise caused by an external reason. In this case, the light emitting unit 311 can employ a semiconductor laser, a titanium sapphire laser, a light emitting diode or the like, however, the embodiment is described on the basis of an example of the light emitting probe main body 310 employing a light emitting unit 311 provided with a light emitting diode.

Further, the detection unit 411 is provided with a detection portion 415, a lock amplifier 416 and a logarithmic amplifier 417 which are shown in the balloon in the center upper side of FIG. 2. In this case, the detection unit 411 can employ a photoelectric conversion element such as a photodiode, a photomultiplier tube or the like, however, this embodiment is described on the basis of an example of the detection probe main body 410 employing a detection unit 411 provided with a photodiode.

On the other hand, the biological light measuring device main body 10 is structured such as to include a calculating machine 11, a display portion 12 and a main body communication portion 13. In this embodiment, the biological light measuring device main body 10 and the probe device 100 can be electrically connected in a cordless manner by respectively providing the main body communication portion 13 and the probe communication portion 552 in the biological light measuring device main body 10 and the probe device 100. Accordingly, since the test subject having the probe device 100 installed at the head portion is electrically connected to the biological light measuring device main body 10 without being connected via a cord, it is possible to measure a test result of the test subject by the biological light measuring device main body 10 without being constrained by the cords. Further, a control command signal from the main body side is received by the probe communication portion 552 provided within the control board, the control signal is transmitted to each of the probe control boards 243 from the control portion within the main control board 242, and the probe control boards 243 individually control each of the detection units 411 and the light emitting units 311 on the basis of the control signal.

In accordance with the biological light measuring device 1, a weak near infrared beam (the light) of about 1.5 mW emitted from the light source portion 316 by receiving the power source supply from the power source portion 560 of the electronic board 502 is focused within the light source portion 316 by using a lens system (not shown), and is irradiated to the head portion of the test subject 50 via the optical fiber 413 for irradiation of the projection portion 412 provided in the lower portion of the light source portion 316. The light emitted from the light source portion 316 is intensity modulated at an optional frequency f about 100 Hz to 10 MHz by the oscillator 315 for removing noise caused by an external reason.

A wavelength of the used light depends on a spectral characteristic of a target material in the living body, and is used by selecting one wavelength or a plurality of wavelengths from the light of a wavelength range between 600 nm and 1400 nm in the case of measuring an oxygen saturation and a blood volume on the basis of concentrations of Hb and HbO2 in the blood. The light irradiated to the head portion of the test subject 50 passes through a region of a visual field of the optical fiber 413 for irradiation, passes through a region in which the blood dynamic state is locally changed such as the blood or the like in the region, and is detected by the detection portion 415 via the optical fiber 413 for detecting of the projection portion 412 formed in the lower portion of the detection unit 411.

The light detected by the detection unit 411 via the optical fiber 413 for detection is photoelectrically converted in the detection unit 411, and an intensity of the passing light is output as a strength of the electric signal. In the electric signal expressing the intensity of the passing light output from a plurality of detection units 411, only a light intensity modulation frequency component of the light source is extracted by the lock amplifier 416, and is collected to the main control board 242 from the probe control board 243 via the wiring sheet 240 after being logarithmically transformed by the logarithmic amplifier 417.

The signal collected by a plurality of detection units 411 is input to the differential amplifier 550 of the main control board 242. In this differential amplifier 550, for example, an output from a detection probe 400a is input to a negative pole, and an output from a detection probe 400b is input to a positive pole. As a result, a differential signal of the intensities of the passing lights at two different positions is output as an output signal. The output signal from the differential amplifier 550 is converted into a digital signal by the A/D converter 551 sequentially, and is transmitted to the biological light measuring device main body 10 via the probe communication portion 552.

The signal received by the biological light measuring device main body 10 via the main body communication portion 13 is incorporated into the calculating machine 11 so as to be processed, and is thereafter displayed as time-series data in the display portion 12. In this case, in this embodiment, there is employed the structure in which the main body communication portion 13 and the probe communication portion 552 are of the wireless communication system, however, the signal may be sent and received via an infrared ray or other communication means. Of course, they may be connected via a cord, however, in this case, freedom of the behavior of the test subject is constrained.

Further, in this embodiment, as illustrated in a balloon in the lower side of FIG. 2, the sheet-shaped probe holding body 200 is constructed by an outer sheet 221 provided on an outer surface of the probe holding body 200, an inner sheet 222 provided on an inner surface on the head portion side of the test subject of the probe holding body 200, and a light shielding sheet 223 provided between the outer sheet 221 and the inner sheet 222. In this embodiment, the outer sheet 221 and the inner sheet 222 are constructed by a stereoscopic textile formed by a resin fiber formed in a range of thickness between 5 mm and 10 mm.

The stereoscopic textile is generally called a three-dimensional textile, and corresponds to a textile obtained by stereoscopically organizing a fiber material (filament formed) in three directions including vertical, lateral and perpendicular directions, and a raw material of a connecting fiber, and may employ any fiber of a polyester fiber manufactured from polyethylene terephthalate, polybutylene terephthalate, polytrimethylene terephthalate or the like, a cellulose fiber such as cotton, cuprammonium rayon, viscose rayon, purified cellulose fiber or the like, a polyamide fiber manufactured from nylon 6, nylon 66 or the like, and the like. A mode of the fiber may employ any fiber of a filament yarn and a spanning yarn.

In this embodiment, it is possible to firmly hold the light emitting probe attaching portion 350 or the detection probe attaching portion 450 while achieving a weight saving thereof with the suitable thickness, by employing the stereoscopic textile, and it is possible to improve the passage of the perspiration of the test subject via the space formed in the textile.

On the other hand, the light shielding sheet 223 is structured such as to improve a poorness of the light shielding characteristic of the probe holding body 200 formed by the stereoscopic textile, and in this embodiment, a cloth of a black resin fiber is inserted between the outer sheet 221 and the inner sheet 222. It is possible to prevent the outside light from making an intrusion into the probe holding portion 220 by employing the light shielding sheet 223, and it is possible to expect an effect of absorbing the reflected light reflected from the scalp so as to improve a measuring performance.

Further, in this embodiment, the wiring sheet 240 is arranged in such a manner as to be laminated on the probe holding body 200, however, it may be incorporated in an inner portion of the laminated structure. Specifically, since it is possible to prevent the wiring from being disconnected by a disturbance, by arranging it in a layer which is inside the outer sheet 221, it is preferable to arrange it at this position. It is possible to prevent the wiring sheet 240 from being unnecessarily bent by being arranged between the outer sheet 221 and the inner sheet 222, and it is possible to prevent disconnection. Further, the wiring sheet 240 employs, for example, a band-shaped flexible printed circuit board structured by attaching a copper foil or the like to a surface of a thin resin film. Accordingly, it is possible to achieve a laminated structure in which the wiring is applied without generating a thickness unevenness of the probe holding body 200.

Further, in this embodiment, the probe holding body 200 is formed in a curved stereoscopic shape in conformity to the curved shape of the head portion of the test subject, by thermally crimping the probe holding body 200.

Further, in this embodiment, there is employed a structure of "surface contact including a plurality of points" in which a plurality of sub-projection portions 414 are arranged around the main projection portion 412 of the detection probe main body 410.

The light emitting probe and the detection probe in accordance with the prior art employ a "one point contact" system such that the contact surface 60 with the test subject 50 is provided with a structure reinforcing the fiber for irradiation or detection directly or by the projection portion. Accordingly, there is a problem that it is hard to maintain the leading end portion of the optical fiber provided so as to protrude to the leading end portion of each of a plurality of probe main bodies attached to the probe holder in a vertical attitude with respect to the subcutaneous part of the head portion. In the prior art, there is a structure in which the attitude of the leading end portion of the optical fiber can be changed by being provided with a fine adjustment knob, however, there is a problem that it takes a long time to adjust the vertical attitude of a lot of probes.

In this embodiment, since the contact with the surface of the living body (the contact surface 60) of the test subject 50 is structured such as to be provided with the main projection portion 412 having the light transmitting means (the fiber 313 for irradiation or the fiber 413 for detection) communicating the light irradiating means (the light emitting unit 311) or the light detecting means (the detection unit 411) with the external portion in its axis, and a plurality of sub-projection portions 414 protruding to the periphery of the main projection portion 412 and having approximately the same length, it is possible to easily support the light transmitting means on the surface of the living body in the vertical attitude.

In this embodiment, as illustrated in the balloon in the lower side of FIG. 2, since it is possible to suppress a slope in four directions, by setting four sub-projection portions 414 on concentric circles P1 and P2 of the main projection portion 412 at uniform intervals, it is possible to lighten the problem of the prior art.

Particularly, in this embodiment, since the protruding dimension of the probe holding body 200 to the upper portion is formed short, and the distance between the probe holding body 200 and the surface of the living body (the contact surface 60) is formed long, via the sheet holding portion 500, the light emitting probe 300 and the detection probe 400 attached to the probe holding body 200 are hard to have the leading end of the main projection portion 412 closely attached to the surface of the living body (the contact surface 60). In this regard, in this embodiment, since it is possible to suppress the slope in four directions by means of the sub-projection portions 414, it is possible to solve the problem mentioned above.

In this case, if three or more sub-projection portions 414 exist around the main projection portion 412, the detection probe main body 410 provided with the sub-projection portions 414 stands on its own feed in the vertical attitude, so that it is possible to expect the same effect mentioned above.

Further, in this embodiment, it is possible to be tender to the test subject 50 and easily achieve the vertical attitude of the detection probe main body 410, by forming the sub-projection portions 414 of a flexible resin material, a somewhat soft material such as a rubber, an elastomer or the like. The light emitting probe 300 can obtain the same operation and effect by being provided with the same structure as mentioned above.

Further, in this embodiment, the main projection portion 412 and a plurality of sub-projection portions 414 are supported so as to be rotatable around the main projection portion 412. In this kind of biological light measuring device, there is a problem that the hair on the surface of the living body obstructs and it is hard to closely attach the leading end of the optical fiber to the surface of the living body of the test subject 50. However, in the prior art, since the contact point between the probe and the subcutaneous part of the head portion comes to "one point contact", the leading end portion of the optical fiber pushes the hair aside so as to adjust. Accordingly, there is a problem that it takes a long time to adjust the vertical attitude of a lot of probes while pushing the hair aside.

In this embodiment, since the light emitting probe main body 310 and the detection probe main body 410 provided with the main projection portion 412 and the sub-projection portions 414 are supported so as to be rotatable around the main projection portion 412, the leading ends of the sub-projection portions 414 push the hair aside by rotating the sub-projection portions 414. Accordingly, it is easy to closely attach the leading end portion of the fiber 413 for detection to the surface of the living body. Further, since the sub-projection portions 414 rotate around the main projection portion 412, it is possible to easily achieve the vertical attitude of the detection probe main body 410.

Further, since the sub-projection portions 414 having the flexibility rotate around the main projection portion 412 having a greater strength than the sub-projection portions 414 by forming the sub-projection portions 414 by the flexible material and by providing the fiber 413 for detection at their axis, it is possible to easily push the hair aside and control the attitude. In addition, in this embodiment, since the second stage of sub-projection portions 414 is provided around the main projection portion 412, it is possible to push the hair aside even if the rotating range is reduced.

In this case, the light emitting probe 300 can obtain the same operation and effect by being provided with the same structure, as mentioned above.

Further, in this embodiment, it is possible to rotate the light emitting probe main body 310 and the detection probe main body 410 via a cap portion 700 by making the light emitting probe main body 310 and the detection probe main body 410 exposed to the outer surface of the probe holding body 200, and attaching the cap portion 700 to the exposed position. Accordingly, since it is possible to rotate the probe device 100 by taking hold of the cap portion 700 exposed to the outer surface of the probe holding body 200 with the fingers or the like even in a state in which the probe device 100 is attached to the test subject, it is possible to easily rotate the sub-projection portions 414. Accordingly, it is possible to easily push the hair aside and change the attitude.

Further, in this embodiment, a signal connector 418 is provided in a portion in which the light emitting probe main body 310 and the detection probe main body 410 are covered by the cap portion 700. Accordingly, it is possible to easily achieve a wire connection by attaching and detaching the cap portion 700. Further, since the wire connection is not affected by the rotation of the light emitting probe main body 310 and the detection probe main body 410, the disconnection is not frequently generated. Further, since the wire connection portion is covered by the cap portion 700, the falling of the wire connection portion is not generated, and the beauty is improved.

Further, in this embodiment, the light emitting probe main body 310 and the detection probe main body 410 are constructed by a first casing 421 provided with the light emitting unit 311 or the detection unit 411, and a second casing 422 rotatably attached to the periphery of the first casing 421. The first casing 421 is provided with the main projection portion 412 and the sub-projection portions 414, and the second casing 422 is detachably attached to the light emitting probe attaching portion 350 or the detection probe attaching portion 450.

In accordance with this structure, it is possible to rotate the first casing 421 provided with the main projection portion 412 and the sub-projection portions 414, and it is possible to attach and detach the detection probe main body 410 constituted by the first casing 421 and the second casing 422 from the detection probe attaching portion 450.

Further, since the second casing 422 is provided with a spring body 423, it is possible to slidably move the first casing 421 via the spring body 423 in a direction of the test subject. Accordingly, it is possible to improve a degree of adhesion of a surface contact including a plurality of point contacts in conformity to concavity and convexity of the head portion of the test subject.

Figure 3:
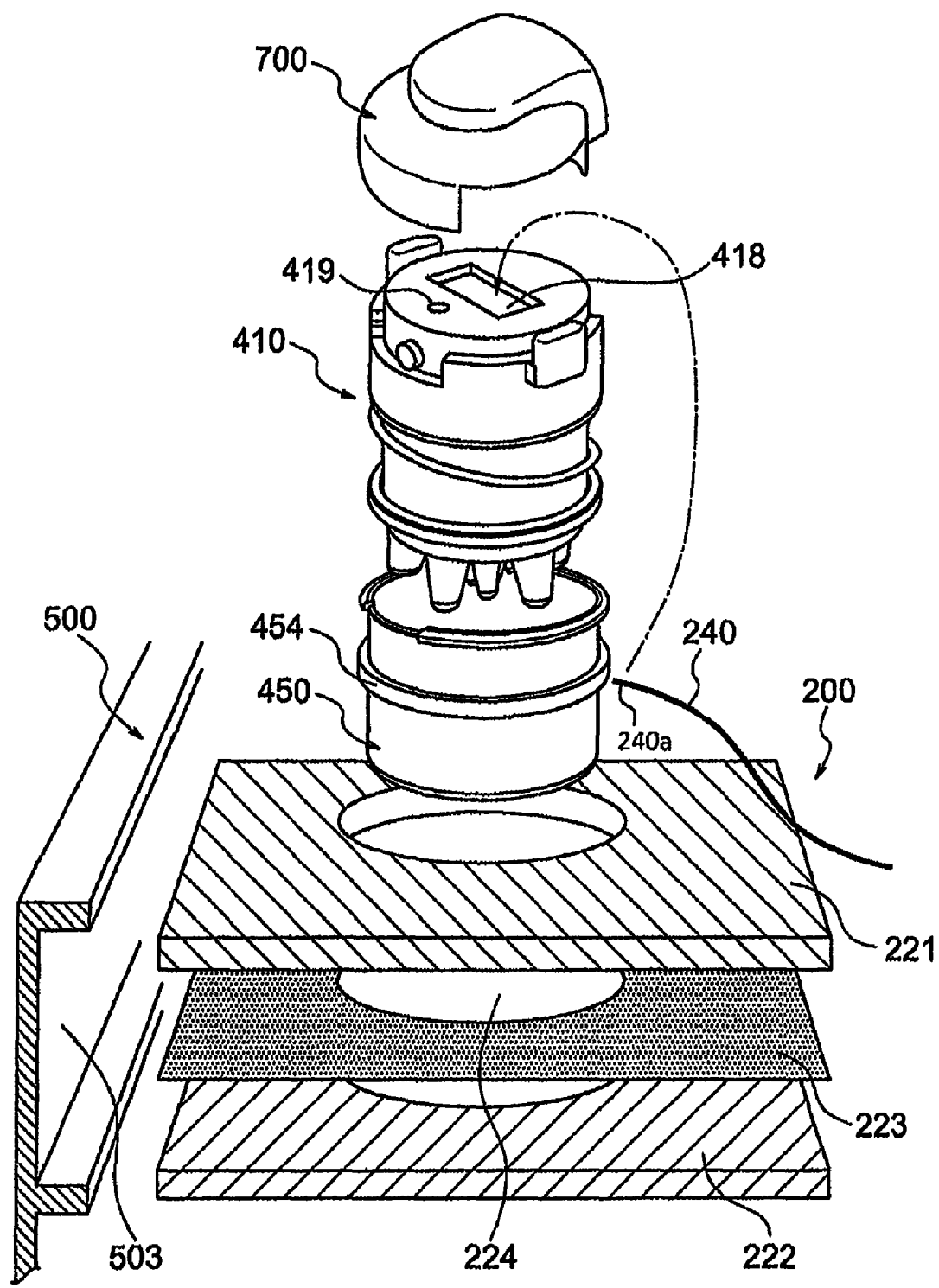
FIG. 3 is an expansion plan view of a peripheral structure of a detection probe.
Figure 4:
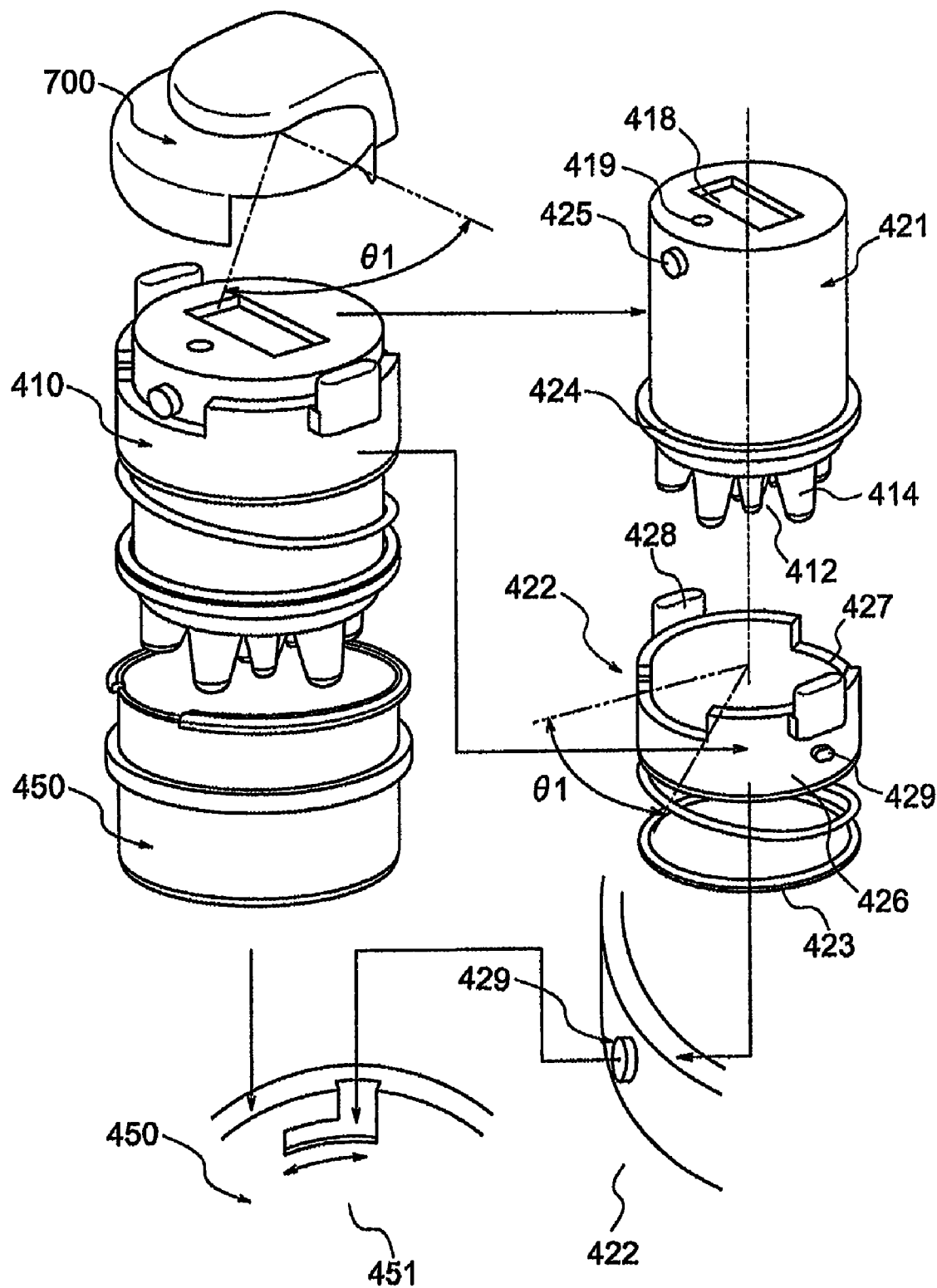
FIG. 4 is an expansion plan view of the peripheral structure of the detection probe.
Figure 5:
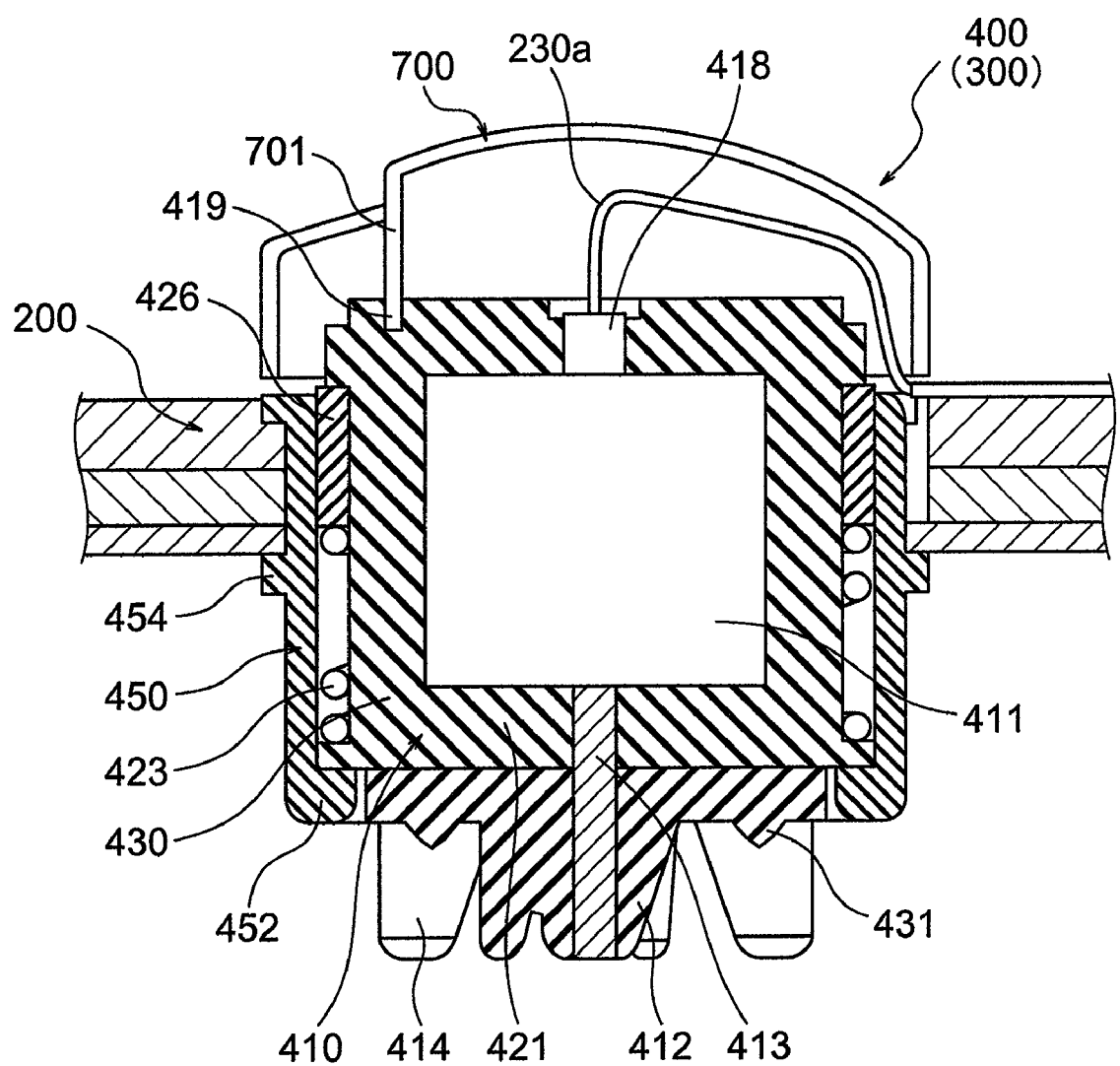
FIG. 5 is a cross-sectional view of the detection probe.
Figure 6A:
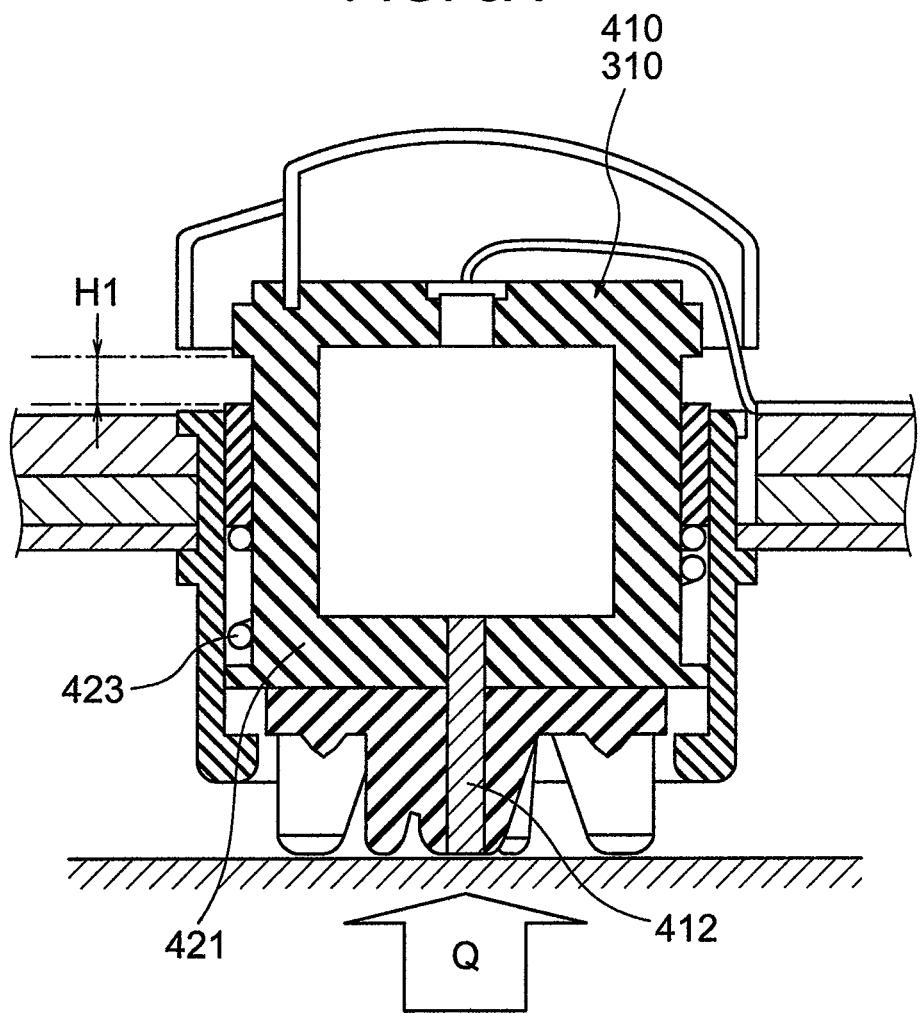
FIGS. 6A to 6C are explanatory views of a telescopic mechanism of the detection probe.
Figure 6B:
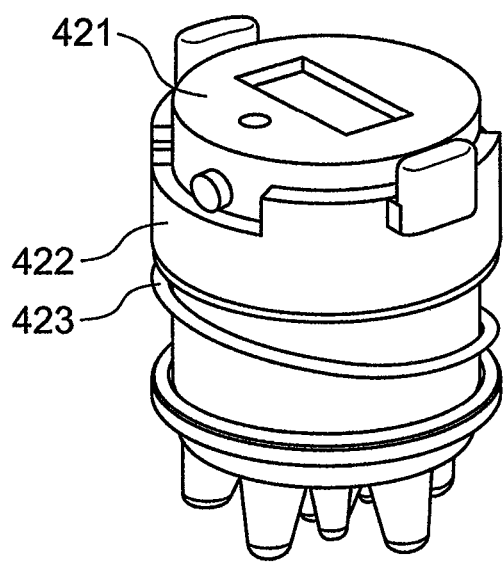
Figure 6C:
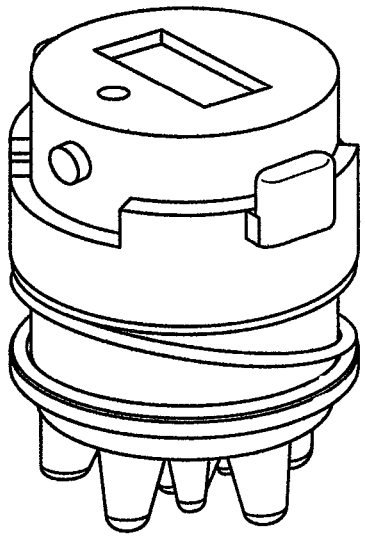
Figure 7A:
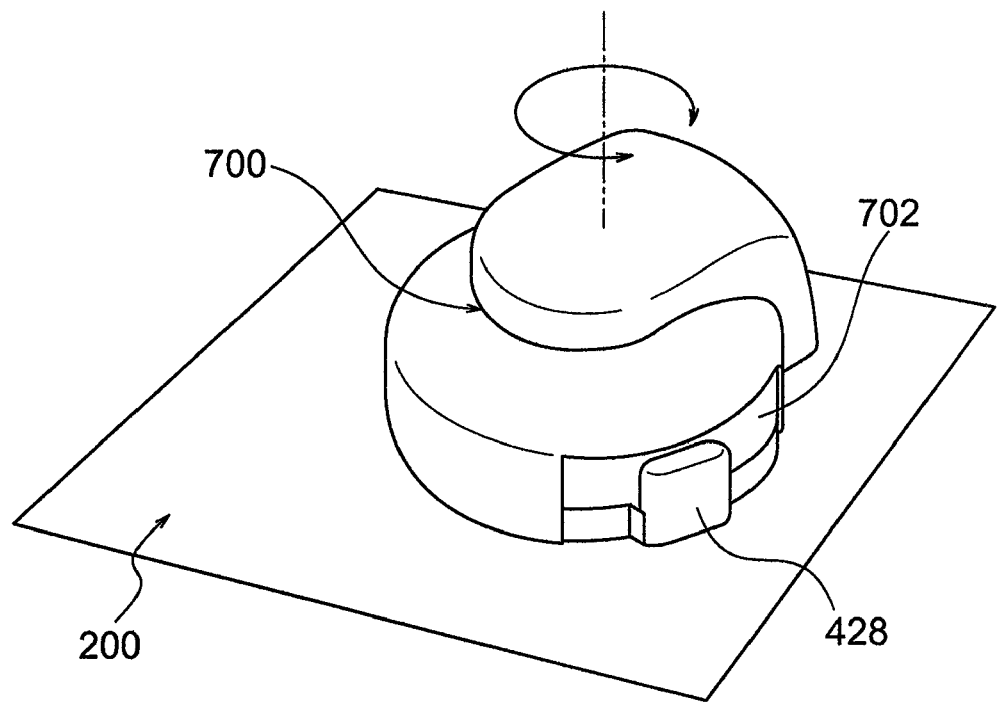
FIGS. 7A and 7B are explanatory views of a rotating state of the detection probe.
Figure 7B:
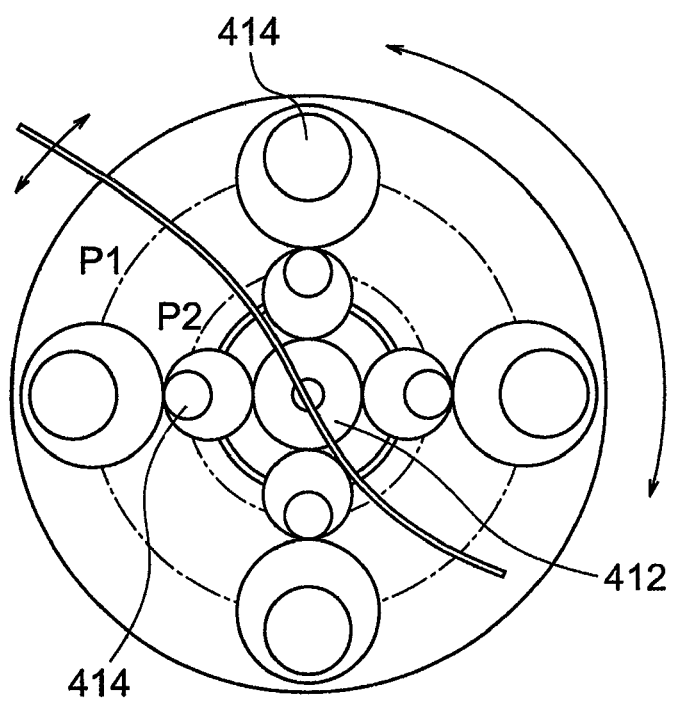

Next, a description will be given further in detail of a peripheral structure of the detection probe with reference to FIGS. 3 to 7 (7A and 7B). FIG. 3 is an expansion plan view of the peripheral structure of the detection probe. FIG. 4 is an expansion plan view of the peripheral structure of the detection probe. FIG. 5 is a cross-sectional view of the detection probe. FIGS. 6A to 6C are explanatory views of a telescopic mechanism of the detection probe. FIGS. 7A and 7B are explanatory views of a rotating state of the detection probe, in which FIG. 7A is a perspective view of an outer appearance, and FIG. 7B is a bottom elevational view. In this case, as mentioned above, since the light emitting probe 300 is provided with the same structure as the detection probe 400, a description thereof will be omitted here.

In FIG. 3, the probe holding body 200 is provided with a plurality of opening portions 224 for attaching the detection probe attaching portion 450 to a predetermined position. Further, the probe holding body 200 is provided with a laminated structure having the light shielding sheet 223 between a pair of outer sheet 221 and inner sheet 222.

In this case, in this embodiment, the detection probe attaching portion 450 is provided with a low tubular outer appearance, a pair of ring-shaped flange portions 454 protruding to an outer periphery are provided in one end side, and the opening portions 224 are fitted and fixed between the pair of flange portions 454.

In this embodiment, the outer sheet 221, the inner sheet 222 and the light shielding sheet 223 in which the opening portions 224 are previously formed, are prepared at a time of assembling, and they are aligned by the opening portions 224 in this order so as to be thermally crimped and bonded. Further, in the case that the wiring sheet 240 is interposed between the inner sheet and the outer sheet at a time of bonding, the wiring sheet 240 is easily bonded to the detection probe 400 later by making a wire connection terminal of the wiring sheet 240 exposed from the opening portion 224 so as to thermally crimp.

The probe holding body 200 cut into a predetermined magnitude peripherally is inserted into a joint groove 503 formed in an inner side of the sheet holding portion 500 in its peripheral end portion so as to be fixed by an adhesive agent or the like. At a time of fixing, the other end of the wiring sheet 240 is bonded to the electronic board 502.

On the other hand, the detection probe main body 410 (the light emitting probe main body 310) is detachably attached to the detection probe attaching portion 450 (the light emitting probe attaching portion 350) fixed to a predetermined position of the probe holding body 200. Further, the detection probe main body 410 attached to the detection probe attaching portion 450 connects a wire connection terminal 240a of the wiring sheet 240 to a signal connector 418 provided in its upper portion.

Further, a cap attaching hole 419 is provided in an upper portion of the detection probe main body 410 so as to be adjacent to the signal connector 418, and the cap portion 700 can be attached by inserting a connection rod 701 (refer to FIG. 5) formed in the cap portion 700 to the cap attaching hole 419.

Next, a description will be given of a specific structure of the detection probe main body 410 and an attaching structure of the detection probe attaching portion 450, with reference to FIGS. 4 to 7. In FIG. 4, the detection probe main body 410 is constructed by the first casing 421 having a columnar tubular shape, and the second casing 422 arranged in the periphery thereof.

In FIG. 4, the first casing 421 is provided with the signal connector 418 and the cap attaching hole 419 in an upper surface of the columnar shape, and is provided with the main projection portion 412 and a plurality of sub-projection portions 414 in a lower surface of the columnar shape. Further, a flange 424 protruding to an outer side is formed in a lower end portion of a peripheral side surface of the columnar shape, and a pair of projection portions 425 are provided at opposing positions in an upper end portion of the peripheral side surface.

On the other hand, the second casing 422 is constructed by a tubular outer peripheral casing 426 and a coil-shaped spring body 423. Concave portions 427 which are formed lower are formed at opposing positions in an upper end portion of the outer peripheral casing 426, and grip portions 428 protruding to an outer side and an upper side (toward a center axis) are formed at a position which is deviated at 90 degrees from the concave portions 427. The grip portions 428 can be utilized as a finger grip portion for attaching and detaching the detection probe main body 410 and the detection probe attaching portion 450.

Further, the first casing 421 and the second casing 422 are assembled in such a manner that the spring body 423 is inserted to an outer periphery of the first casing 421, the outer peripheral casing 426 is next inserted, and the spring body 423 and the outer peripheral casing 426 are sandwiched and held between the flange 424 and the projection portions 425. In accordance with this structure, one end of the spring body 423 is fixed to the flange 424, and the other end acts in such a manner as to press the outer peripheral casing 426 to the projection portions 425 side. On the other hand, the outer peripheral casing 426 is prevented by the projection portions 425 from being moved to one end side, however, since the spring body 423 is expanded and contracted to the other end side, it is possible to slidably move the first casing 421.

Further, a pair of fixed projections 429 are provided at opposing positions in an outer periphery of the outer peripheral casing 426. On the other hand, an L-shaped connection groove 451 extending from an upper end to a downward side and further extending sideways is formed in an inner surface of the detection probe attaching portion 450. In accordance with this structure, it is possible to fix the detection probe main body 410 to the detection probe attaching portion 450 by inserting the assembled detection probe main body 410 in such a manner that the fixed projection 429 of the outer peripheral casing 426 comes into line with the connection groove 451 of the detection probe attaching portion 450 and rotating.

As mentioned above, in this embodiment, since the detection probe main body 410 can be easily attached to and detached from the detection probe attaching portion 450, it is easy to maintain the detection probe main body 410.

Further, in this embodiment, since the projection portions 425 provided in a peripheral side surface of the first casing 421 are fitted to the concave portions 427 of the outer peripheral casing 426, and the projection portions 425 move on the concave portions 427 in a circumferential direction, the first casing 421 can rotate the detection probe main body 410. Accordingly, the detection probe main body 410 can be rotated in such a manner as to oscillate in a range of an angle θ1 in the circumferential direction of the concave portions 427. This is because if the rotating range is set free, a fault is generated in the wire connection between the signal connector 418 and a connecting terminal 230a, and the motion of pushing the hair aside and the attitude change of the detection probe main body 410 can sufficiently achieve their purpose on the basis of the oscillating motion.

In FIG. 5, in the tubular detection probe attaching portion 450, an inward protruding flange 452 is formed in a lower end portion of its inner surface. Since the outer peripheral casing 426 is fixed to the detection probe attaching portion 450, whereby the detection probe attaching portion 450 is fixed to the detection probe main body 410, the first casing 421 slidably moving with respect to the outer peripheral casing 426 acts in such a manner as to always press the lower end of the first casing 421 to the flange 452.

On the contrary, as shown in FIGS. 6A to 6C, if a pressure Q is applied from the test subject side, it acts such that the spring body 423 is contracted as shown in FIG. 6C from a state in which the spring body 423 is expanded as shown in FIG. 6B. Accordingly, as shown in FIG. 6A, the first casing 421 is moved upward, and acts in such a manner as to absorb the pressure Q from the test subject side. Therefore, each of a plurality of detection probe main bodies 410 and the light emitting probe main bodies 310 can closely attach the leading end of the main projection portion 412 of the detection probe main body 410 and the light emitting probe main body 310 to the scalp of the test subject in conformity to the concavity and convexity of the head portion of the test subject. As a result, since each of the first casing 421 protrudes upward at H1 with respect to the detection probe attaching portion 450 so as to absorb the pressure Q, it is possible to fit a whole of the probe device 100 to the head portion of the test subject.

Turning back to FIG. 5, the first casing 421 is separated into a main casing 430 provided with the detection unit 411, and a cushion material portion 431 provided with the main projection portion 412 and the sub-projection portions 414. The cushion material portion 431 is formed by a soft material, and can come into contact with the scalp of the test subject without paining. Further, the cushion material portion 431 is attached to the main projection portion 412 by an adhesive material, and can be replaced as consumable goods.

Further, as shown in FIG. 7B, each sub-projection portion 414 is formed as an inverted circular truncated cone shape having a roundness in a vertex, and is formed in such a manner as to be opened toward an outer side from an inner side. Accordingly, it acts in such a manner as to always closely attaching the leading ends of a plurality of sub-projection portions 414 to the scalp of the test subject. In other words, it is possible to activate the detection probe main body 410 in such a manner as to stand on its feet with respect to the scalp of the test subject. This self-subsistence can be more actuated by rotating the detection probe main body 410. In this case, in this embodiment, since the outer sub-projection portions 414 more greatly contribute to the control of the attitude of the detection probe main body 410, the outer sub-projection portions 414 are formed thicker than the inner sub-projection portions 414. Further, the inner sub-projection portions 414 fill up between the outer sub-projection portions 414 and the main projection portion 412, and the structure of "surface contact including a plurality of points" is achieved by the main projection portion 412 and the sub-projection portions 414. Accordingly, the leading end of the main projection portion 412 can be closely attached to the scalp by putting the detection probe main body 410 on foot without paining the test subject, and pushing the hair existing within "surface contact" aside by rotating the sub-projection portions 414 so as to improve a pushing efficiency.

Turning back to FIG. 5, the cap portion 700 is formed as a dome shape in its cross-sectional shape, and a connection rod 701 is formed so as to be hung downward from an inner surface thereof. Accordingly, if the cap portion 700 is grasped by fingers so as to be rotated, the rotating force can rotate the sub-projection portion 414 provided in the first casing 421 on the basis of the connection between the connection rod 701 and the cap attaching hole 419. In this case, the wiring terminal 230a is incorporated into the cap portion 700 via a gap between the cap portion 700 and the detection probe main body 410 so as to be connected to the signal connector 418.

Further, as shown in FIGS. 7A and 7B, in the cap portion 700, notch portions 702 are formed on both sides thereof in such a manner as to avoid the pair of grip portions 428 provided in the second casing 422. The notch portions 702 are formed in the same manner as the angle θ1 in the circumferential direction of the concave portions 427 of the second casing 422, as described in FIG. 4. Further, as shown in FIG. 7A, in accordance with the notch portions 702 provided with the magnitude of the angle θ1, the pair of notch portions 702 can be formed as a suitable shape to grasp the cap portion 700 by a thumb and an index finger.

On the other hand, since it is possible to easily pick the pair of grip portions 428 arranged so as to be fitted to the notch portions 702 by the thumb and the index finger, by forming the notch portions 702 in the cap portion 700, it is possible to easily attach and detach the detection probe main body 410 to and from the detection probe attaching portion 450 by rotating the detection probe main body 410.

Next, a description will be given of a particular structure of the board holding portion main body 1100 constructing the board holding portion 241 holding the electronic board 1000 such as the probe control board 243, the main control board 242 and the like, with reference to FIGS. 8A and 8B.

Figure 8A:
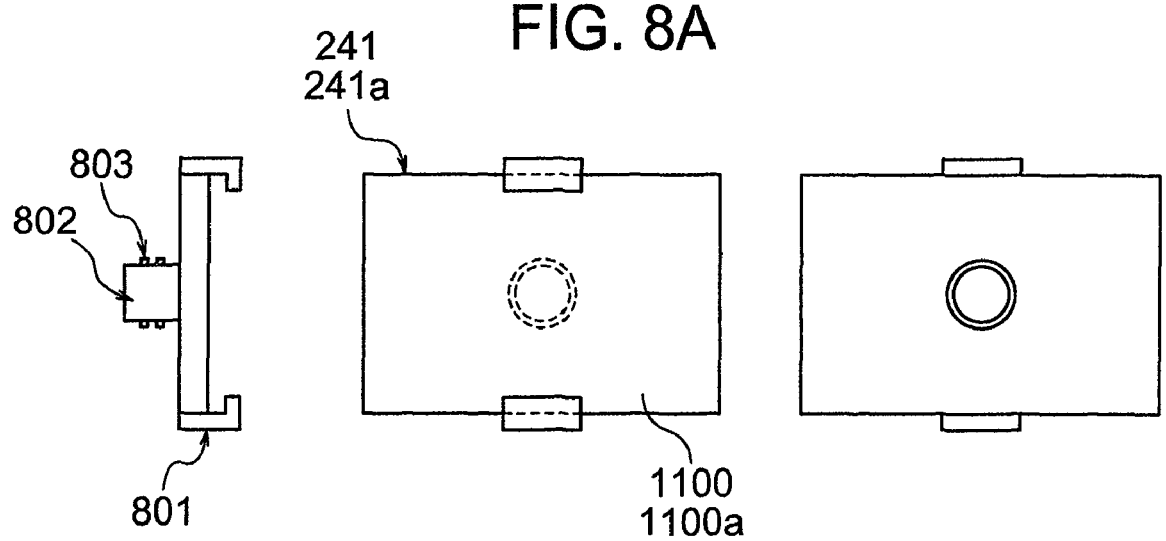
FIGS. 8A and 8B are views showing an example of a board holding member.

FIG. 8A is a view showing one example of a board holding portion main body 1100a of the first board holding portion 241a holding the probe control board 243, and shows a left side elevational view, a front elevational view and a back elevational view from the left of the paper surface. In this case, reference numeral 801 denotes a claw portion for holding the board. The claw portion 801 prevents the board from coming down and uselessly moving at a time when the probe device is installed to the test subject. In this case, the structure is made such as to have the claw portion 801, however, the board can be of course held by interposing an adhesive member such as an adhesive agent or the like between the board and the holding member.

Further, reference numeral 802 denotes a joint portion to the board attaching portion 1101. The joint portion 802 is structured such that the joint portion 802 is fitted to the hole portion 305 (refer to FIG. 9C) of the board attaching portion 1101. In this case, reference numeral 803 denotes a fixing member for fixing and holding to the probe holding body 200. As mentioned above, in this embodiment, it is possible to firmly fix the board holding portion main body 1100a to the probe holding body 200 by fitting the board holding portion main body 1100a to the board attaching portion 1101, and it is possible to stably install the probe device 100 even in a state of holding the electronic board 1000.

As mentioned above, since the board holding portion main body 1100 can be fitted to the board attaching portion 1101, it is possible to install the board holding portion 241 only to the portion having the test subject position to be tested. In the example in FIG. 1, the board holding portion 241 is structured such as to be sequentially arranged in the highest row; however, it may be arranged in a lower stage or a middle stage.

However, since it is possible to efficiently get a heat generated from the electronic board 1000 itself out by arranging the board in the highest stage, and it is possible to prevent an influence of a noise in the heat of the detection probe 400, it is desirable to arrange the electronic board 1000 at least in the upper side than the detection probe 400.

Further, it is possible to reduce the thickness by fitting and arranging the board holding portion main body 1100 to the board attaching portion 1101, in comparison with the case that the electronic board 1000 is arranged so as to lap over the probe. Further, in the present embodiment, since the first board holding portions 241a holding the probe control boards 243 are arranged regularly alternately, a weight balance can be kept, and an installing characteristic is improved. Since the installing characteristic is improved as mentioned above, it is possible to suppress a stagger of the main body, and it is possible to secure a stability of measurement.

Figure 8B:
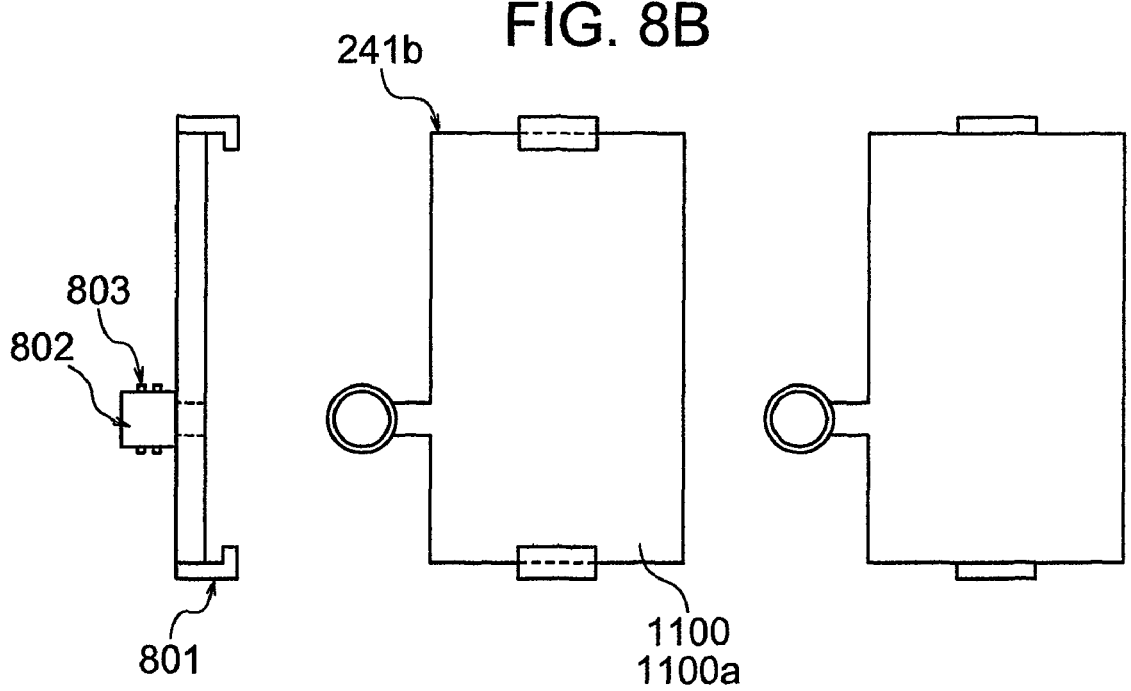

FIG. 8B shows the second board holding portion 241b holding the main control board 242. This is the same structure as FIG. 8A, however, since the main control board 242 is larger than the probe control board 243, it is preferable to arrange the main control board 242 on the side of the probe holding body 200. Accordingly, it is detachably connected in such a manner as to fit to the terminal hole portion 305 in the matrix-shaped hole portions 305 formed in the probe holding body 200. Alternatively, it may be detachably connected in such a manner as to fit to the attaching portion in the terminal end of the light emitting probe attaching portion 350 or the detection probe attaching portion 450 arranged in the matrix shape. Further, the portion holding the main control board 242 is formed in a lateral direction from the joint portion, and the same claw portion 801 as FIG. 8A is further provided.

Further, although not being illustrated, the sub-projection portions 414 may be attached to the leading end of the joint portion 802 of the board holding portion 241. Since it is possible to more closely fix to the scalp of the test subject by attaching the sub-projection portions 414, a stability is improved.

Figure 9A:
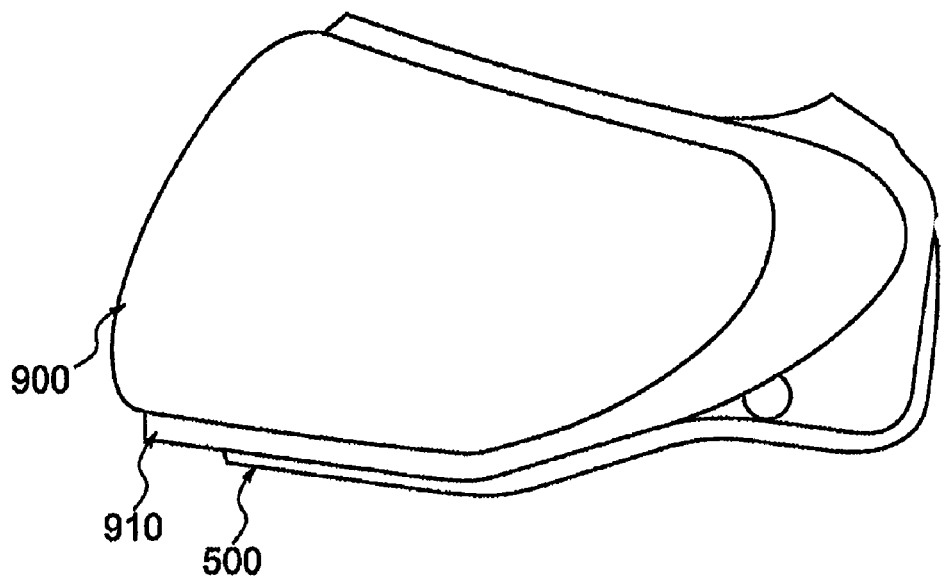
FIGS. 9A to 9C are outline views at a time of installing a protection cover to the probe device.
Figure 9B:
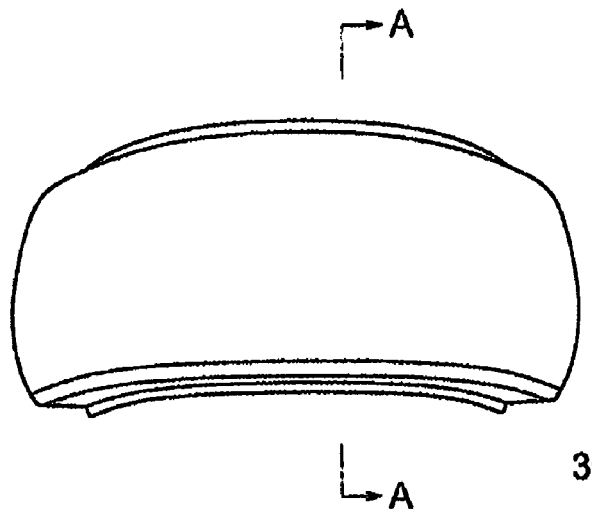
Figure 9C:
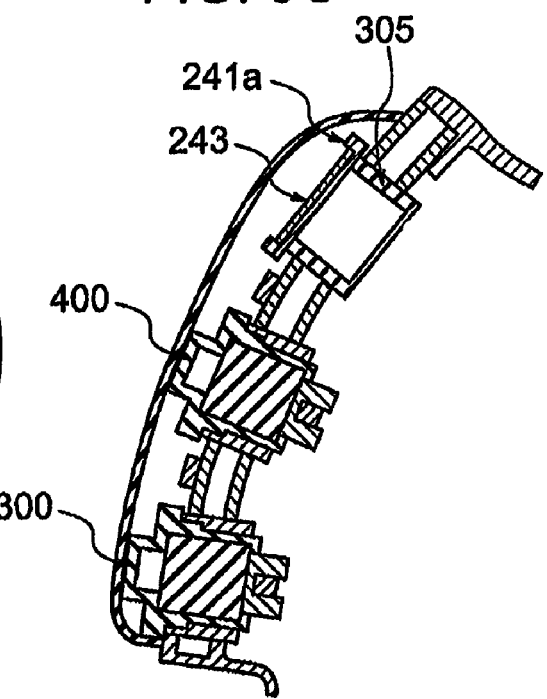

FIGS. 9A to 9C are views showing one example of a protection cover 900 for protecting the probe and the board installed to the probe device 100. FIG. 9A is a side elevational view at a time of installing the protection cover 900 to the probe device 100. The protection cover is formed by a rubber-like member, a plastic member or the like having a flexibility and formed as a stereoscopic textile structure or a mesh shape. Further, reference numeral 910 denotes a protection cover frame, whereby it is possible to shut off light from the external portion. The protection cover frame 910 and the probe device 100 may be bonded by forming concavity and convexity in the probe device side 100 and the protection cover frame 910 side, respectively, and fitting them, or may be bonded by forming a concave portion capable of fitting the protection cover 910 itself in the probe device so as to fit. Further, it is possible to detachably fix them by a magic tape, a screw, an adhesive agent or the like.

FIG. 9B is a front elevational view of a state in which the protection cover 900 is installed to the probe device 100, and FIG. 9C is a cross-sectional view along a line A-A in FIG. 9A. FIG. 9C is a cross-sectional view of a state in which the protection cover 900 is installed to the probe device 100, the probe control board 243 held by the board holding portion 241a from the upper stage is attached to the hole portion 305, the light receiving portion 400 is attached to the middle stage thereof, and the light emitting portion 300 is attached to the lower stage thereof.

It is possible to prevent a damage caused by a shock from the external portion and a drop of the board and the probe, which corresponds to a disturbance element, by setting the protection cover 900. Further, since it is possible to shut off the outside light by installing the protection cover, a detection sensitivity is improved.

Figure 10A:
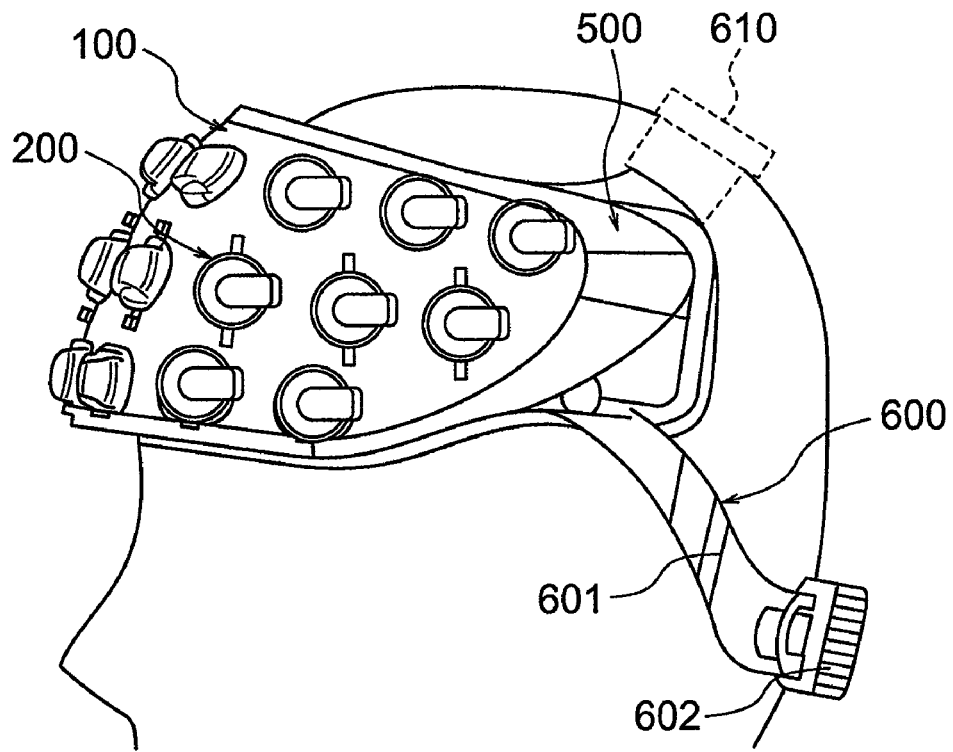
FIGS. 10A and 10B are views showing an optical fiber attaching structure of the probe device.
Figure 10B:
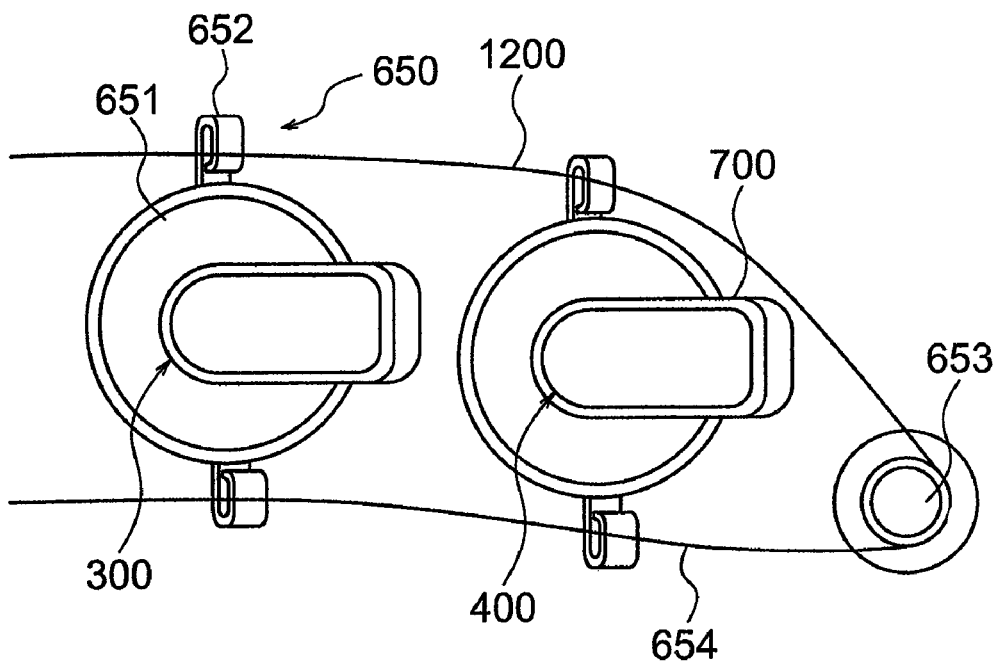
Figure 11A:
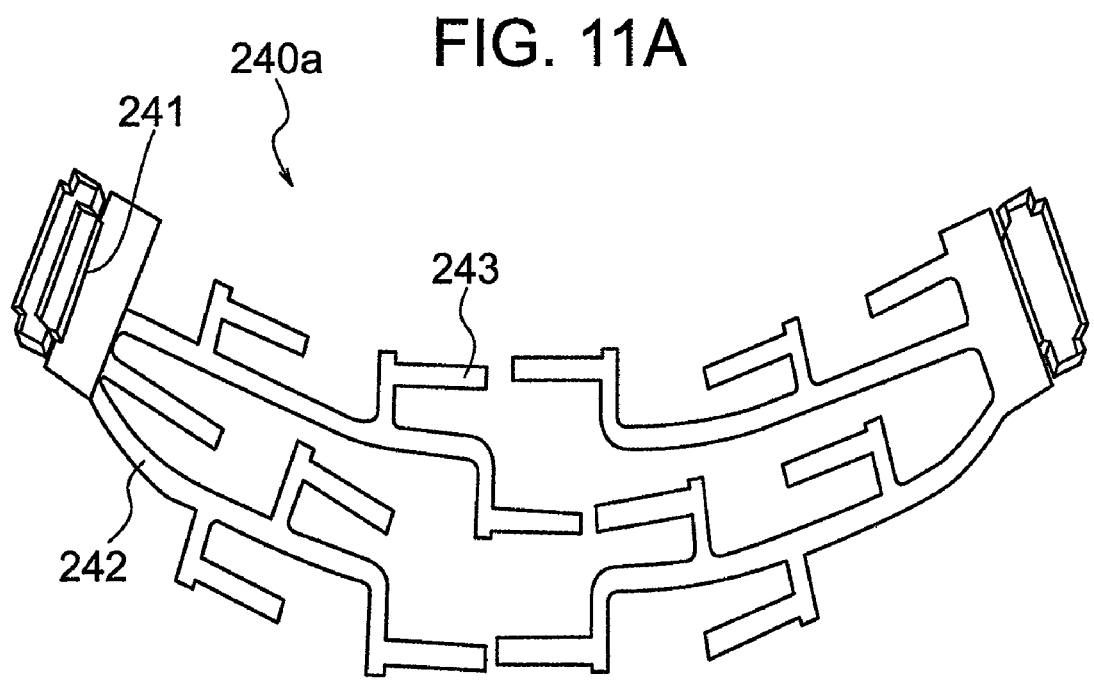
FIGS. 11A and 11B are views showing an application example of a wiring sheet.
Figure 11B:
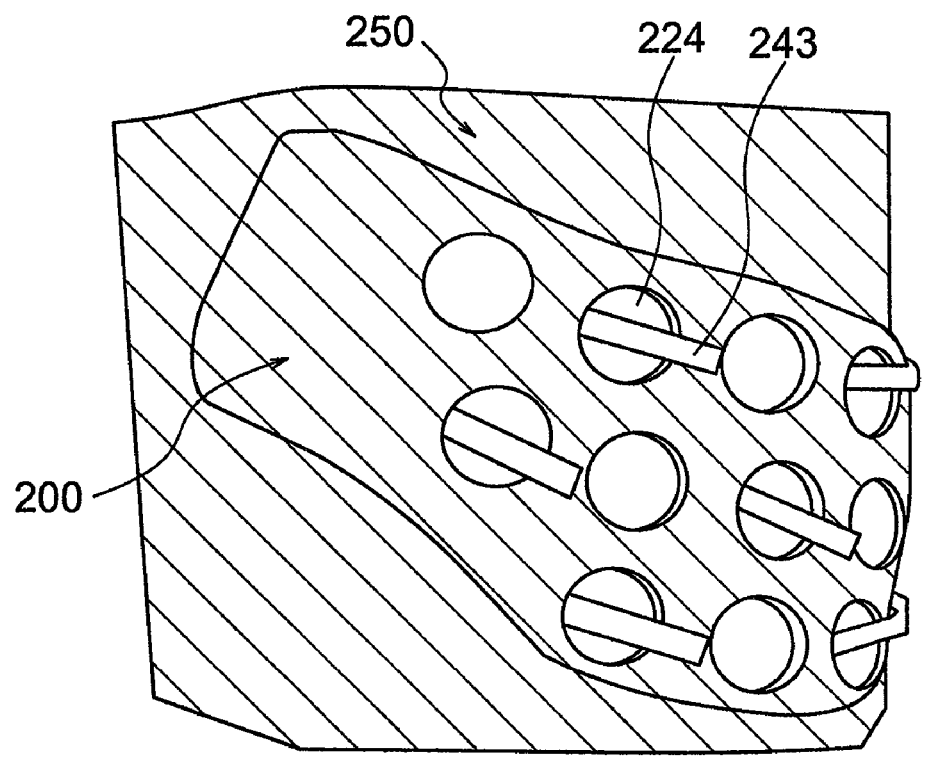

Next, a description will be given of another application of the probe device 100 in accordance with another embodiment with reference to FIGS. 10A, 10B, 11A and 11B. FIGS. 10A and 10B are explanatory views of a state in which the optical fiber is used as the light source, FIG. 11A is a side elevational view of a used state, and FIG. 11B is a partly enlarged view. FIGS. 11A and 11B are outer appearance views showing the other application of the wiring sheet, in which FIG. 11A is an outer appearance view of the wiring sheet, and FIG. 11B is an explanatory view of an assembled state of the wiring sheet.

First of all, in FIGS. 10A and 10B, in the embodiment mentioned above, the description is given of the structure in which the light emitting probe 300 employs the light emitting unit 311 provided with the light emitting diode, however, a light emitting probe main body (not shown) to which an optical fiber transmitting an externally generated light source is connected may be attached in place of the light emitting probe main body 310 provided with the light emitting unit 311. In this case, it is not necessary to largely change the other structures by wiring an optical fiber 1200 in place of the wiring terminal 230a (refer to FIG. 5A). However, there is a problem that the optical fiber 1200 is conducted to each of the light emitting probes 300, however, in this case, it is possible to wire the optical fiber in order by preparing a fastening adapter 650 and attaching the optical fiber 1200, as shown in FIGS. 10A and 10B.

In this case, a description will be given of a structure in a state in which the optical fiber 1200 is wired in the probe device 100, with reference to FIGS. 10A and 10B. As shown in FIG. 10B, in this embodiment, the fastening adapter 650 provided with an optical fiber holding projection portion 652 is prepared on both ends of a flat ring-shaped washer member 651, and is attached to the flange portions 454 together with the probe holding body 200, or the light emitting probe 300 and the detection probe 400 in the middle stage are attached at a time of attaching the cap portion 700. Further, an optical fiber attaching portion 653 is provided in the sheet holding portion 500 to which a belt 601 is attached, and an optical fiber 654 put through the optical fiber attaching portion 653 is attached to the optical fiber attaching portion 653.

Further, this embodiment is structured such that one end of the belt 601 is attached to the sheet holding portion 500 somewhat on a lower side. Accordingly, it is possible to improve an installing characteristic of the sheet holding portion 500 by positioning a belt fixing portion 602 at the rear side of a neck of the test subject. Further, in this embodiment, as a means for further improving the installing characteristic of the probe device 100, a second fixing band portion 610 may be attached to the sheet holding portion 500 somewhat on an upper side (refer to the broken line portion). In accordance with the second fixing band portion 610, it is possible to fix the probe device 100 on the upper side of the head portion of the test subject. Accordingly, since it is possible to securely hold the probe device 100 via three points surrounding the head portion of the test subject, that is, the front portion of the head portion by the sheet holding portion 500, the rear portion of the neck by the fixing band portion 600 and the above of the rear portion of the head portion by the second fixing band portion 610, by attaching these two fixing band portions, it is effective in the test at a time of operating which has a risk of it coming down.

Further, in FIGS. 11A and 11B, the wiring sheet 240a in accordance with this embodiment is constituted by the wiring sheet 240 for the probe device of the type introducing the light source generated in the outer portion of the probe device 100 to the light emitting probe 300 via the optical fiber.

In the case of always using the light emitting probe main body using the external light source, the wiring sheet 240 wired from the probe control board 243 attached to the upper stage of the probe holding body 200 is not necessary. Accordingly, it is preferable to employ the wiring sheet 240 which is exclusive to the detection probe 400 shown in FIG. 11A.

At this time, since the probe control board 243 is not necessary, a measuring object range is widened and a wide range measurement can be achieved, by detaching the first board holding portion 241a from the probe holding body 200 and newly attaching the detection probe 400 and the light emitting probe in the matrix shape. Further, it is sufficient to newly install the corresponding electronic board 1000 without detaching the board holding portion 241 holding the main control board 242, or install the wiring sheet 240 to the electronic board 502 and the main control board 242 in the case of a convertible electronic board 1000.

As mentioned above, since the light emitting probe 300 can use the same probe holding body in both of the mode using the light emitting diode and the mode using the optical fiber, it is possible to measure under an optimum condition in correspondence to an intended use.

Further, the wiring sheet 240 employed in the first embodiment and the wiring sheet 240a are previously formed along a spherical surface in such a manner as to be aligned with the probe holding body 200 formed as a curve. The description here is given of the wiring sheet 240, however, this structure can be employed in the wiring sheet 240a.

The probe device 100 in accordance with this embodiment is formed in a curved manner so as to be fitted to the spherical shape of the head portion of the test subject. Particularly, it is necessary to form the probe holding body 200 as the curved shape with the laminated structure. Accordingly, in this embodiment, the wiring sheet 240 which is previously formed along the spherical surface, as shown in FIG. 11A.

The wiring sheet 240a is formed so as to be provided with a pair of right and left structures in the same manner as the wiring sheet 240. The wiring sheet 240a is structured such that several band-like branch members 262 are drawn out of a base member 261 formed in an end portion, and the branch members 262 are further branched off. The branched end portions 263 are formed as a narrow paper tablet shape, and are formed so as to be exposed from an opening portion 224 of the probe holding body 200.

In accordance with this embodiment, a curved metal mold (not shown) is previously prepared, the inner sheet 222, and the light shielding sheet 223, the wiring sheet 240 and the outer sheet 221 are positioned in the metal mold in this order and via the opening portion 224, are laminated in such a manner that the end portion 242 of the wiring sheet 240 is exposed from the opening portion 224, and are molded by thermally crimping. At a time of molding, the inner sheet 222, the light shielding sheet 223 and the outer sheet 221 are easily deformed from a flat sheet-shaped textile to the stereoscopic textile because they are constituted by the textile, however, there is a problem that the normal wiring sheet to which the wiring is applied cannot correspond to the molding, and a molding defect such as a seamed state is generated.

However, since the wiring sheet 240a in accordance with this embodiment is previously molded in conformity to the spherical surface, and is constructed by a plurality of branched structures, it is possible to form the molded product 250 in which the end portion 242 is exposed from the opening portion 224, as shown in FIG. 11B. The molded product 250 can form the probe holding body 200 by cutting the periphery out.

It should be further understood by those skilled in the art that although the foregoing description has been made of embodiments of the invention, the invention is not limited thereto and various changes and modifications may be made without departing from the spirit of the invention and the scope of the appended claims.

The invention claimed is:

1. A probe device comprising:
a flexible probe holding body;
a plurality of light emitting probes and a plurality of detection probes;
a board holding portion attached to said probe holding body;
an electronic board attached to said board holding portion;
a sheet holding portion adapted for holding said probe holding body at a predetermined position of a head portion of the living body;
a plurality of probe attaching portions;
a plurality of board attaching portions; and
a fixing band portion for attaching said sheet holding portion to the living body,
wherein said electronic board comprises:
a plurality of probe control boards for controlling the plurality of light emitting probes and the plurality of detection probes within a predetermined region; and
a main control board for controlling said plurality of probe control boards and communicating with the other devices, and
wherein said board holding portion comprises:
a first board holding portion for attaching the probe control board; and
a second board holding portion for attaching the main control board,
wherein the probe holding body has a plurality of hole portions arranged at a predetermined interval,
the board attaching portion and the probe attaching portions are fitted to the hole portions,
the light emitting probes and the detection probes are detachably fitted to the probe attaching portions;

the board holding portion is detachably fitted to the board attaching portions; and wherein the structure of each of the probe attaching portions are configured to allow the board holding portion to detachably fit to the probe attaching portions and the structure of each of the board attaching portions are configured to allow the light emitting probes and the detection probes to detachably fit to the board attaching portions.

2. A probe device as claimed in claim 1, wherein said main control board has a communication means configured to communicate wirelessly with a biological light measuring device main body to image process an electric signal output from said probe device to display a map.

3. A probe device as claimed in claim 1, wherein said main control board is provided in an end portion of said probe holding body.

4. A probe device as claimed in claim 3, wherein the probe device is provided with an electronic board having a power source portion configured to supply power to said probe device.

5. A probe device as claimed in claim 4, wherein said main control board and said electronic board are arranged to oppose each other.

6. A probe device as claimed in claim 1, wherein the sheet holding portion is arranged to hold said probe holding body at a predetermined position of a surface of the living body, said sheet holding portion surrounds a periphery of said probe holding body, and forms a shielding space shielding light while being provided with a predetermined gap between said probe holding body and the surface of the living body.

7. A probe device as claimed in claim 1, wherein each of said plurality of light emitting probes and each of said plurality of detection probes are provided with respective probe main bodies each including a light emitting unit or a detection unit, and said probe attaching portion is configured to freely rotate said probe main body around a main projection portion in such a manner that one end provided with said main projection portion and a sub projection portion is exposed to a shielding space between the probe holding body and the head portion and the other end is exposed to an outer side of the probe holding body.

8. A probe device as claimed in claim 1, wherein a wiring sheet is arranged in such a manner as to be laminated on said probe holding body, and is provided with a protection cover covering said probe holding body in a state in which said probe control board, said control board and said wiring sheet are attached.

9. The probe device accordingly to claim 1,
wherein a structure of the plurality of board attaching portions and the plurality of probe attaching portions are of the same shape.

* * * * *